(12) United States Patent
Pinter et al.

(10) Patent No.: US 9,264,664 B2
(45) Date of Patent: Feb. 16, 2016

(54) SYSTEMS AND METHODS FOR DYNAMIC BANDWIDTH ALLOCATION

(75) Inventors: Marco Pinter, Santa Barbara, CA (US); Justin Chan, Bellevue, WA (US)

(73) Assignee: INTOUCH TECHNOLOGIES, INC., Goleta, CA (US)

(*) Notice: Subject to any disclaimer, the term of this patent is extended or adjusted under 35 U.S.C. 154(b) by 1228 days.

(21) Appl. No.: 12/959,550

(22) Filed: Dec. 3, 2010

(65) Prior Publication Data

US 2012/0144336 A1    Jun. 7, 2012

(51) Int. Cl.
| | |
|---|---|
| G06F 15/16 | (2006.01) |
| H04N 7/15 | (2006.01) |
| H04L 29/06 | (2006.01) |
| G06F 19/00 | (2011.01) |
| H04M 3/56 | (2006.01) |

(52) U.S. Cl.
CPC .............. *H04N 7/15* (2013.01); *G06F 19/3418* (2013.01); *H04L 65/403* (2013.01); *H04L 65/80* (2013.01); *H04M 3/567* (2013.01)

(58) Field of Classification Search
CPC ..... H04N 7/15; H04M 3/567; G06F 19/3418; H04L 65/403; H04L 65/80
USPC ........................................................ 709/232
See application file for complete search history.

(56) References Cited

U.S. PATENT DOCUMENTS

| | | | |
|---|---|---|---|
| 3,821,995 | A | 7/1974 | Aghnides |
| 4,107,689 | A | 8/1978 | Jellinek |
| 4,213,182 | A | 7/1980 | Eichelberger et al. |
| 4,413,693 | A | 11/1983 | Derby |
| 4,471,354 | A | 9/1984 | Smith |
| 4,519,466 | A | 5/1985 | Shiraishi |
| 4,553,309 | A | 11/1985 | Hess et al. |
| 4,572,594 | A | 2/1986 | Schwartz |
| 4,625,274 | A | 11/1986 | Schroeder |
| 4,638,445 | A | 1/1987 | Mattaboni |
| 4,652,204 | A | 3/1987 | Arnett |

(Continued)

FOREIGN PATENT DOCUMENTS

| | | |
|---|---|---|
| AU | 1216200 A | 5/2000 |
| CA | 2289697 | 11/1998 |

(Continued)

OTHER PUBLICATIONS

Fulbright et al., "SWAMI: An Autonomous Mobile Robot for Inspection of Nuclear Waste of Storage Facilities", Autonomous Robots, vol. 2, 1995, pp. 225-235.
"Appeal from the U.S. District Court for the Central District of California in No. 11-CV-9185, Judge Percy Anderson", May 9, 2014, pp. 1-48.
"Google translation of: Innovations Report", From research project to television star: Care-O-bot in ZDF series, available online at <http://www.innovations-report.de/specials/printa.php?id=5157>, Sep. 28, 2001.
"MPEG File Format Summary", downloaded from: <http://www.fileformat.info/format/mpeg/egff.htm>, Feb. 1, 2001, 8 pages.

(Continued)

*Primary Examiner* — Joseph E Avellino
*Assistant Examiner* — James Conaway

(57) ABSTRACT

Disclosed herein are various embodiments of systems and methods that may be utilized in a variety of videoconferencing applications. According to various embodiments, techniques may be utilized to dynamically allocate and adjust bandwidth utilization during a videoconferencing session. A data network may allow for the transmission of data between two or more endpoints. The data exchanged between the endpoints may include video data, audio data, control data, and status data. Control data may be utilized in various embodiments to operate a robotic videoconferencing endpoint. Accordingly, various components of a data network connecting videoconferencing endpoints may transmit data wirelessly.

13 Claims, 8 Drawing Sheets

(56) References Cited

U.S. PATENT DOCUMENTS

| | | |
|---|---|---|
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, III et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey |
| 5,374,879 A | 12/1994 | Pin |
| 5,375,195 A | 12/1994 | Johnston |
| 5,400,068 A | 3/1995 | Ishida et al. |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,153,833 B1 | 8/1995 | Gordon et al. |
| 5,441,042 A | 8/1995 | Putman |
| 5,441,047 A | 8/1995 | David |
| 5,442,728 A | 8/1995 | Kaufman et al. |
| 5,462,051 A | 10/1995 | Oka et al. |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | DeVault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober et al. |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |

(56) References Cited

U.S. PATENT DOCUMENTS

| | | | |
|---|---|---|---|
| 6,314,631 B1 | 11/2001 | Pryor | |
| 6,317,652 B1 | 11/2001 | Osada | |
| 6,317,953 B1 | 11/2001 | Pryor | |
| 6,321,137 B1 | 11/2001 | De Smet | |
| 6,324,184 B1 | 11/2001 | Hou et al. | |
| 6,324,443 B1 | 11/2001 | Kurakake et al. | |
| 6,325,756 B1 | 12/2001 | Webb et al. | |
| 6,327,516 B1 | 12/2001 | Zenke | |
| 6,330,486 B1 | 12/2001 | Padula | |
| 6,330,493 B1 | 12/2001 | Takahashi et al. | |
| 6,346,950 B1 | 2/2002 | Jouppi | |
| 6,346,962 B1 | 2/2002 | Goodridge | |
| 6,369,847 B1 | 4/2002 | James et al. | |
| 6,373,855 B1* | 4/2002 | Downing et al. | 370/468 |
| 6,381,515 B1 | 4/2002 | Inoue et al. | |
| 6,389,329 B1 | 5/2002 | Colens | |
| 6,400,378 B1 | 6/2002 | Snook | |
| 6,408,230 B2 | 6/2002 | Wada | |
| 6,411,055 B1 | 6/2002 | Fujita et al. | |
| 6,430,471 B1 | 8/2002 | Kintou et al. | |
| 6,430,475 B2 | 8/2002 | Okamoto | |
| 6,438,457 B1 | 8/2002 | Yokoo | |
| 6,445,964 B1 | 9/2002 | White et al. | |
| 6,449,762 B1 | 9/2002 | McElvain | |
| 6,452,915 B1 | 9/2002 | Jorgensen | |
| 6,457,043 B1 | 9/2002 | Kwak et al. | |
| 6,459,955 B1 | 10/2002 | Bartsch et al. | |
| 6,463,352 B1 | 10/2002 | Tadokoro et al. | |
| 6,463,361 B1 | 10/2002 | Wang | |
| 6,466,844 B1 | 10/2002 | Ikeda et al. | |
| 6,468,265 B1 | 10/2002 | Evans et al. | |
| 6,470,235 B2 | 10/2002 | Kasuga et al. | |
| 6,474,434 B1 | 11/2002 | Bech | |
| 6,480,762 B1 | 11/2002 | Uchikubo et al. | |
| 6,491,701 B2 | 12/2002 | Tierney | |
| 6,496,099 B2 | 12/2002 | Wang et al. | |
| 6,496,755 B2 | 12/2002 | Wallach et al. | |
| 6,501,740 B1 | 12/2002 | Sun et al. | |
| 6,507,773 B2 | 1/2003 | Parker et al. | |
| 6,522,906 B1 | 2/2003 | Salisbury et al. | |
| 6,523,629 B1 | 2/2003 | Buttz et al. | |
| 6,526,332 B2 | 2/2003 | Sakamoto et al. | |
| 6,529,620 B2 | 3/2003 | Thompson | |
| 6,529,765 B1 | 3/2003 | Franck | |
| 6,529,802 B1 | 3/2003 | Kawakita et al. | |
| 6,532,404 B2 | 3/2003 | Colens | |
| 6,535,182 B2 | 3/2003 | Stanton | |
| 6,535,793 B2 | 3/2003 | Allard | |
| 6,540,039 B1 | 4/2003 | Yu | |
| 6,543,899 B2 | 4/2003 | Covannon et al. | |
| 6,549,215 B2 | 4/2003 | Jouppi | |
| 6,563,533 B1 | 5/2003 | Colby | |
| 6,567,038 B1 | 5/2003 | Granot et al. | |
| 6,580,246 B2 | 6/2003 | Jacobs | |
| 6,581,798 B2 | 6/2003 | Liff et al. | |
| 6,584,376 B1 | 6/2003 | Van Kommer | |
| 6,587,750 B2 | 7/2003 | Gerbi et al. | |
| 6,590,604 B1 | 7/2003 | Tucker et al. | |
| 6,594,269 B1 | 7/2003 | Polcyn | |
| 6,594,552 B1 | 7/2003 | Nowlin et al. | |
| 6,597,392 B1 | 7/2003 | Jenkins et al. | |
| 6,602,469 B1 | 8/2003 | Maus et al. | |
| 6,604,019 B2 | 8/2003 | Ahlin et al. | |
| 6,604,021 B2 | 8/2003 | Imai et al. | |
| 6,611,120 B2 | 8/2003 | Song et al. | |
| 6,643,496 B1 | 11/2003 | Shimoyama et al. | |
| 6,646,677 B2 | 11/2003 | Noro et al. | |
| 6,650,748 B1 | 11/2003 | Edwards et al. | |
| 6,666,374 B1 | 12/2003 | Green et al. | |
| 6,667,592 B2 | 12/2003 | Jacobs et al. | |
| 6,674,259 B1 | 1/2004 | Norman et al. | |
| 6,684,129 B2 | 1/2004 | Salisbury et al. | |
| 6,691,000 B2 | 2/2004 | Nagai et al. | |
| 6,693,585 B1 | 2/2004 | MacLeod | |
| 6,710,797 B1 | 3/2004 | McNelley et al. | |
| 6,724,823 B2 | 4/2004 | Rovati et al. | |
| 6,728,599 B2 | 4/2004 | Wright et al. | |
| 6,763,282 B2 | 7/2004 | Glenn et al. | |
| 6,764,373 B1 | 7/2004 | Osawa et al. | |
| 6,769,771 B2 | 8/2004 | Trumbull | |
| 6,781,606 B2 | 8/2004 | Jouppi et al. | |
| 6,784,916 B2 | 8/2004 | Smith | |
| 6,785,589 B2 | 8/2004 | Eggenberger et al. | |
| 6,791,550 B2 | 9/2004 | Goldhor et al. | |
| 6,798,753 B1 | 9/2004 | Doganata et al. | |
| 6,799,065 B1 | 9/2004 | Niemeyer | |
| 6,799,088 B2 | 9/2004 | Wang et al. | |
| 6,804,580 B1 | 10/2004 | Stoddard et al. | |
| 6,804,656 B1 | 10/2004 | Rosenfeld et al. | |
| 6,810,411 B1 | 10/2004 | Coughlin et al. | |
| 6,816,192 B1 | 11/2004 | Nishikawa | |
| 6,816,754 B2 | 11/2004 | Mukai et al. | |
| 6,836,703 B2 | 12/2004 | Wang et al. | |
| 6,839,612 B2 | 1/2005 | Sanchez et al. | |
| 6,840,904 B2 | 1/2005 | Goldberg | |
| 6,845,297 B2 | 1/2005 | Allard | |
| 6,852,107 B2 | 2/2005 | Wang et al. | |
| 6,853,878 B2 | 2/2005 | Hirayama et al. | |
| 6,853,880 B2 | 2/2005 | Sakagami et al. | |
| 6,871,117 B2 | 3/2005 | Wang et al. | |
| 6,879,879 B2 | 4/2005 | Jouppi et al. | |
| 6,888,333 B2 | 5/2005 | Laby | |
| 6,892,112 B2 | 5/2005 | Wang et al. | |
| 6,893,267 B1 | 5/2005 | Yueh | |
| 6,895,305 B2 | 5/2005 | Lathan et al. | |
| 6,898,484 B2 | 5/2005 | Lemelson et al. | |
| 6,914,622 B1 | 7/2005 | Smith et al. | |
| 6,925,357 B2 | 8/2005 | Wang et al. | |
| 6,951,535 B2 | 10/2005 | Ghodoussi et al. | |
| 6,952,470 B1 | 10/2005 | Tioe | |
| 6,957,712 B2 | 10/2005 | Song et al. | |
| 6,958,706 B2 | 10/2005 | Chaco et al. | |
| 6,965,394 B2 | 11/2005 | Gutta et al. | |
| 6,990,112 B1* | 1/2006 | Brent et al. | 370/401 |
| 6,995,664 B1 | 2/2006 | Darling et al. | |
| 7,007,235 B1 | 2/2006 | Hussein et al. | |
| 7,011,538 B2 | 3/2006 | Chang | |
| 7,015,934 B2 | 3/2006 | Toyama et al. | |
| RE39,080 E | 4/2006 | Johnston | |
| 7,030,757 B2 | 4/2006 | Matsuhira et al. | |
| 7,053,578 B2 | 5/2006 | Diehl et al. | |
| 7,055,210 B2 | 6/2006 | Keppler et al. | |
| 7,058,689 B2 | 6/2006 | Parker et al. | |
| 7,092,001 B2 | 8/2006 | Schulz | |
| 7,096,090 B1 | 8/2006 | Zweig | |
| 7,115,102 B2 | 10/2006 | Abbruscato | |
| 7,117,067 B2 | 10/2006 | McLurkin et al. | |
| 7,123,285 B2 | 10/2006 | Smith et al. | |
| 7,123,974 B1 | 10/2006 | Hamilton | |
| 7,123,991 B2 | 10/2006 | Graf et al. | |
| 7,127,325 B2 | 10/2006 | Nagata et al. | |
| 7,129,970 B2 | 10/2006 | James et al. | |
| 7,133,062 B2 | 11/2006 | Castles et al. | |
| 7,142,945 B2 | 11/2006 | Wang et al. | |
| 7,142,947 B2 | 11/2006 | Wang et al. | |
| 7,151,982 B2 | 12/2006 | Liff | |
| 7,154,526 B2 | 12/2006 | Foote et al. | |
| 7,155,306 B2 | 12/2006 | Haitin et al. | |
| 7,156,809 B2 | 1/2007 | Quy | |
| 7,158,859 B2 | 1/2007 | Wang et al. | |
| 7,158,860 B2 | 1/2007 | Wang et al. | |
| 7,158,861 B2 | 1/2007 | Wang et al. | |
| 7,161,322 B2 | 1/2007 | Wang et al. | |
| 7,162,338 B2 | 1/2007 | Goncalves et al. | |
| 7,164,969 B2 | 1/2007 | Wang et al. | |
| 7,164,970 B2 | 1/2007 | Wang et al. | |
| 7,167,448 B2 | 1/2007 | Wookey et al. | |
| 7,171,286 B2 | 1/2007 | Wang et al. | |
| 7,174,238 B1 | 2/2007 | Zweig | |
| 7,181,455 B2 | 2/2007 | Wookey et al. | |
| 7,184,559 B2 | 2/2007 | Jouppi | |
| 7,188,000 B2 | 3/2007 | Chiappetta et al. | |
| 7,199,790 B2 | 4/2007 | Rosenberg et al. | |
| 7,202,851 B2 | 4/2007 | Cunningham et al. | |

(56) References Cited

U.S. PATENT DOCUMENTS

| | | | |
|---|---|---|---|
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | McCall |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | Dirienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Domingues et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 | 2/2013 | Cho et al. |
| 8,400,491 B1 * | 3/2013 | Panpaliya et al. ............ 348/14.12 |
| 8,401,275 B2 | 3/2013 | Wang et al. |
| 8,423,284 B2 | 4/2013 | O'Shea |
| 8,451,731 B1 * | 5/2013 | Lee et al. ........................ 370/235 |
| 8,463,435 B2 | 6/2013 | Herzog et al. |
| 8,503,340 B1 | 8/2013 | Xu |
| 8,515,577 B2 | 8/2013 | Wang et al. |
| 8,527,094 B2 | 9/2013 | Kumar et al. |
| 8,532,860 B2 | 9/2013 | Daly |
| 8,610,786 B2 | 12/2013 | Ortiz |
| 8,612,051 B2 | 12/2013 | Norman et al. |
| 8,639,797 B1 * | 1/2014 | Pan et al. ........................ 709/224 |
| 8,670,017 B2 | 3/2014 | Stuart et al. |
| 8,726,454 B2 | 5/2014 | Gilbert, Jr. et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |
| 2001/0002448 A1 | 5/2001 | Wilson |
| 2001/0010053 A1 | 7/2001 | Ben-Shachar et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0007416 A1 * | 1/2002 | Putzolu ............. H04L 29/06027 709/231 |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |
| 2002/0111988 A1 | 8/2002 | Sato |
| 2002/0120362 A1 | 8/2002 | Lathan et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |

(56) References Cited

U.S. PATENT DOCUMENTS

| | | |
|---|---|---|
| 2002/0183894 A1 | 12/2002 | Wang |
| 2002/0184674 A1 | 12/2002 | Xi et al. |
| 2002/0186243 A1 | 12/2002 | Ellis et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer et al. |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1* | 10/2003 | Wang et al. .................. 700/258 |
| 2003/0199000 A1 | 10/2003 | Valkirs et al. |
| 2003/0206242 A1 | 11/2003 | Choi et al. |
| 2003/0212472 A1 | 11/2003 | McKee |
| 2003/0216833 A1 | 11/2003 | Mukai et al. |
| 2003/0216834 A1 | 11/2003 | Allard |
| 2003/0220541 A1 | 11/2003 | Salisbury et al. |
| 2003/0220715 A1 | 11/2003 | Kneifel et al. |
| 2003/0231244 A1 | 12/2003 | Bonilla et al. |
| 2003/0232649 A1 | 12/2003 | Gizis |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley, Jr. et al. |
| 2004/0010344 A1 | 1/2004 | Hiratsuka |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0119814 A1* | 6/2004 | Clisham ................ H04N 7/141 348/14.08 |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0240981 A1 | 12/2004 | Dothan et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka |
| 2005/0065813 A1 | 3/2005 | Mishelevich et al. |
| 2005/0071046 A1 | 3/2005 | Miyazaki et al. |
| 2005/0073575 A1* | 4/2005 | Thacher et al. ............ 348/14.13 |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |

(56) References Cited

U.S. PATENT DOCUMENTS

| | | |
|---|---|---|
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek, Jr. et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi et al. |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandbeg et al. |
| 2007/0078566 A1 | 4/2007 | Wang et al. |
| 2007/0093279 A1 | 4/2007 | Janik |
| 2007/0112700 A1 | 5/2007 | Den et al. |
| 2007/0116152 A1* | 5/2007 | Thesling .................. 375/326 |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1* | 10/2008 | Thielman et al. ............. 370/235 |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0254657 A1* | 10/2009 | Melnyk .................. H04L 47/10 709/224 |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1* | 3/2010 | Shoemake et al. ......... 348/14.02 |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0278086 A1* | 11/2010 | Pochiraju et al. ............. 370/310 |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1* | 1/2011 | Yellamraju et al. ........... 709/224 |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1* | 3/2011 | Hoffert et al. ................. 709/219 |
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |

(56) References Cited

U.S. PATENT DOCUMENTS

| | | |
|---|---|---|
| 2011/0190930 A1 | 8/2011 | Hanrahan et al. |
| 2011/0193949 A1* | 8/2011 | Nambakam et al. ............ 348/74 |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0245973 A1 | 10/2011 | Wang et al. |
| 2011/0280551 A1 | 11/2011 | Sammon |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1* | 5/2012 | Krishnaswamy ............ 370/252 |
| 2012/0191246 A1 | 7/2012 | Roe et al. |
| 2012/0191464 A1 | 7/2012 | Stuart et al. |
| 2012/0203731 A1* | 8/2012 | Nelson et al. .................. 706/52 |
| 2012/0291809 A1 | 11/2012 | Kuhe et al. |
| 2013/0250938 A1* | 9/2013 | Anandakumar et al. ...... 370/352 |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 92/466492 A2 | 1/1992 |
| EP | 92/488673 A2 | 6/1992 |
| EP | 0981905 B1 | 1/2002 |
| EP | 1262142 A2 | 12/2002 |
| EP | 1304872 A1 | 4/2003 |
| EP | 1536660 A3 | 9/2004 |
| EP | 1536660 A2 | 6/2005 |
| EP | 1573406 A2 | 9/2005 |
| EP | 2005/1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 | 12/2010 |
| EP | 2300930 | 3/2011 |
| EP | 2342651 A1 | 7/2011 |
| GB | 2431261 A | 4/2007 |
| JP | 07-194609 A | 8/1995 |
| JP | 07213753 A | 8/1995 |
| JP | 07248823 A | 9/1995 |
| JP | 07257422 A | 10/1995 |
| JP | 08084328 A | 3/1996 |
| JP | 8320727 A | 12/1996 |
| JP | 97/9267276 A | 10/1997 |
| JP | 09267276 A | 10/1997 |
| JP | 10079097 A | 3/1998 |
| JP | 10288689 A | 10/1998 |
| JP | 11-220706 A | 8/1999 |
| JP | 00032319 A | 1/2000 |
| JP | 049800 A | 2/2000 |
| JP | 079587 A | 3/2000 |
| JP | 196876 A | 7/2000 |
| JP | 00188124 A | 4/2001 |
| JP | 125641 A | 5/2001 |
| JP | 01147718 A | 5/2001 |
| JP | 179663 A | 7/2001 |
| JP | 01198865 A | 7/2001 |
| JP | 01198868 A | 7/2001 |
| JP | 01199356 A | 7/2001 |
| JP | 02000574 A | 1/2002 |
| JP | 046088 A | 2/2002 |
| JP | 00235423 A | 2/2002 |
| JP | 2002/112970 A | 4/2002 |
| JP | 2002/101333 A | 5/2002 |
| JP | 2002/305743 A | 10/2002 |
| JP | 02305743 A | 10/2002 |
| JP | 2002-321180 A | 11/2002 |
| JP | 02355779 A | 12/2002 |
| JP | 2004-181229 A | 7/2004 |
| JP | 524824 T | 8/2004 |
| JP | 261941 A | 9/2004 |
| JP | 2004/289379 A | 10/2004 |
| JP | 028066 A | 2/2005 |
| JP | 2005/059170 A | 3/2005 |
| JP | 2005-111083 A | 4/2005 |
| JP | 2006-508806 A | 3/2006 |
| JP | 2006/508806 A | 3/2006 |
| JP | 2006/109094 A | 4/2006 |
| JP | 2006/224294 A | 8/2006 |
| JP | 2006/246438 A | 9/2006 |
| JP | 2007/081646 A | 3/2007 |
| JP | 2007-232208 A | 9/2007 |
| JP | 2007-316966 A | 12/2007 |
| JP | 2009-125133 A | 6/2009 |
| JP | 2010/064154 A | 3/2010 |
| JP | 2010/532109 A | 9/2010 |
| JP | 2010/246954 A | 11/2010 |
| JP | 246954 A | 11/2010 |
| KR | 2006/0037979 A | 5/2006 |
| KR | 2009/0012542 A | 2/2009 |
| KR | 0019479 A | 2/2010 |
| KR | 0139037 | 12/2010 |
| WO | WO-9306690 A1 | 4/1993 |
| WO | 97/42761 A1 | 11/1997 |
| WO | WO-9851078 A1 | 11/1998 |
| WO | WO-9967067 | 12/1999 |
| WO | 00/25516 A1 | 5/2000 |
| WO | WO-0033726 | 6/2000 |
| WO | 01/31861 A1 | 5/2001 |
| WO | WO-03077745 A1 | 9/2003 |
| WO | 2004/008738 A1 | 1/2004 |
| WO | 2004/012018 A2 | 2/2004 |
| WO | WO-2004075456 A2 | 9/2004 |
| WO | 2006/012797 A1 | 2/2006 |
| WO | 2006/078611 A1 | 4/2006 |
| WO | 2006044847 A2 | 4/2006 |
| WO | 2007/041295 A2 | 4/2007 |
| WO | WO-2007041295 | 4/2007 |
| WO | 2007/041038 A1 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | WO-2010033666 A1 | 3/2010 |
| WO | 2010/047881 A1 | 4/2010 |
| WO | 2010/062798 A1 | 6/2010 |
| WO | 2010/065257 A1 | 6/2010 |

(56) References Cited

FOREIGN PATENT DOCUMENTS

| WO | WO-2010120407 A1 | 10/2010 |
|----|------------------|---------|
| WO | WO-2011028589 A2 | 3/2011 |
| WO | 2011/028589 A3 | 4/2011 |
| WO | 2011/097132 A2 | 8/2011 |
| WO | WO-2011097130 A2 | 8/2011 |
| WO | WO-2011109336 A2 | 9/2011 |
| WO | 2011/097132 A3 | 12/2011 |
| WO | 2011/149902 A2 | 12/2011 |

OTHER PUBLICATIONS

"MPEG-4: a Powerful Standard for Use in Web and Television Environments", by Rob Koenen (KPN Research), downloaded from <http://www.w3.org/Architecture/1998/06/Workshop/paper26>, Jul. 1, 1998, 4 pages.
CMU Course 16X62, "Robot user's manual", (describing the Nomad Scout), Carnegie Mellon University, Feb. 1, 2001, 11 pages.
Panusopone et al., "Performance comparison of MPEG-4 and H.263+ for streaming video applications", Circuits Systems Signal Processing, vol. 20, No. 3, 2001, pp. 293-309.
Schraft et al., "Care-O-botTM: The Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.
Nomadic Technologies, Inc., "Nomad Scout User's Manual", Software Version 2.7, Part No. DOC00004, Jul. 12, 1999, pp. 1-59.
ACM Digital Library Record, Autonomous Robots, vol. 11, No. 1, Table of Content, available at <http://dl.acm.org/citation.cfm?id=591550&picked=prox&cfid=360891374&cftoken=35225929>, Jul. 2001, 2 pages.
Brenner, Pablo, "A Technical Tutorial on the IEEE 802.11 Protocol", BreezeCOM Wireless Communications, Jul. 18, 1996, pp. 1-24.
Library of Congress, "008-Fixed-Length Data Elements (NR)", MARC 21 Format for Classification Data, available at <http://www.loc.gov/marc/classification/cd008.html>, retrieved on Jul. 22, 2014, pp. 1-14.
Paulos et al., "Personal Tele-Embodiment", Chapter 9 in Goldberg et al., Ed., "Beyond Webcams", MIT Press, Jan. 4, 2002, pp. 155-167.
Paulos et al., "Social Tele-Embodiment: Understanding Presence", Autonomous Robots, vol. 11, No. 1, Kluwer Academic Publishers, Jul. 2001, pp. 87-95.
Paulos, Eric John, "Personal Tele-Embodiment", Introductory and Cover Pages from 2001 Dissertation Including Contents table, together with E-mails Relating thereto from UC Berkeley Libraries, as Shelved at UC Berkeley Engineering Library (Northern Regional Library Facility), May 8, 2002, 25 pages (including 4 pages of e-mails).
Paulos, Eric John, "Personal Tele-Embodiment", OskiCat Catalog Record, UCB Library Catalog, Results page and MARC Display, retrieved on Jun. 14, 2014, 3 pages.
Screenshot Showing Google Date for Lemaire Telehealth Manual, Screenshot Retrieved on Dec. 18, 2014, 1 page.
Nomadic Technologies, Inc., "Nomad Scout Language Reference Manual", Software Version: 2.7, Part No. DOC00002, Jul. 12, 1999, 47 pages.
"Making Sense of Bandwidth the NetsenseWay", Network congestion in unmanaged Networks bandwidth Estimation and Adaptation Techniques RADVISION'S Netsense Technology, White Paper, Delivering Visual Experiments, 2010, 7 pgs.
Resam, et al., "Synchronizing Network Probes to avoid Measurement Intrusiveness with the Network Weather Service", 2000, 8 pgs.
Adams, Chris, "Mobile Robotics Research Group", Mobile Robotics Research Group, Edinburgh University, http://www.dai.ed.ac.uk/groups/mrg/MRG.html, Internet, Edinburgh. duplicate of 575084, 2000, pp. 1-2.
Ando, et al., "A Multimedia Self-service Terminal with Conferencing Functions", IEEE, Jul. 5-7, 1995, pp. 357-362.
Android Amusement Corp., "What Marketing Secret . . . Renting Robots from Android Amusement Corp!", (Advertisement), 1982.

Applebome, "Planning Domesticated Robots for Tomorrow's Household", New York Times, http://www.theoldrobots.com/images17/dc17.JPG, Mar. 4, 1982, pp. 21, 23.
Baltus, et al., "Towards Personal Service Robots for the Elderly, Proceedings for the Elderly Workshop on Interactive Robots and Entertainment", Computer Science and Robotics, 2000.
Bar-Cohen, et al., "Virtual reality robotic telesurgery simulations using MEMICA haptic system", Internet, Mar. 5, 2001, pp. 1-7.
Bartholomew, "An Apothecary's Pharmacy", http://classes.bnf.fr/ema/grands/034.htm, pp. 1230-1240.
Bauer, Jeffrey C. et al., "Service Robots in Health Care: The Evolution of Mechanical Solutions to Human Resource Problems", Jun. 2003.
Bauer, John et al., "Remote telesurgical mentoring: feasibility and efficacy", IEEE, 2000, pp. 1-9.
Bischoff, "Design Concept and Realization of the Humanoid Service Robot HERMES", Field and Service Robotics, Springer, London, 1998, pp. 485-492.
Blackwell, Gerry, "Video: A Wireless LAN Killer App?", Internet, Apr. 16, 2002, pp. 1-3.
Breslow, Michael J. et al., "Effect of a multiple-site intensive care unit telemedicine program on clinical and economic outcome an alternative paradigm for intensivist staffing", Critical Care Med; vol. 32 No. 1, Jan. 2004, pp. 31-38.
Brooks, Rodney, "Remote Presence", Abstracts from Flesh & Machines, How Robots Will Change Us, Feb. 2002, pp. 131-147.
Candelas, Herias et al., "Flexible virtual and remote laboratory for teaching Robotics", FORMATEX 2006; Proc. Advance in Control Education Madrid, Spain, Jun. 2006, pp. 21-23.
Celi, et al., "The EICU: It's not just telemedicine", Critical Care Medicine vol. 29, No. 8 (Supplement), Aug. 2001.
Cheetham, Anastasia et al., "Interface Development for a Child's Video Conferencing Robot", 2000, pp. 1-4.
Cleary, et al., "State of the art in surgical robotics: Clinical applications and technology challenges", Internet, Feb. 24, 2002, pp. 1-26.
CNN, "Floating 'droids' to roam space corridors of the future", Internet, Jan. 12, 2000, pp. 1-4.
cnn.com/technology, "Paging R.Robot: Machine helps doctors with patients", Internet, Sep. 30, 2003, 1-3.
Crowley, Susan L., "Hello to Our Future", AARP Bulletin, http://www.cs.cmu.ed/-nursebot/web/press/aarp 99__14/millennium.html, Jan. 2000.
Dalton, "Techniques for Web Telerobotics", PhD Thesis, University of Western Australia, http://telerobot.mech.uwa.edu.au/information.html, http://catalogue.library.uwa.edu.au/search, 2001, 27-62 pp. 149-191.
Davies, "Robotics in Minimally Invasive Surgery", Internet, 1995, pp. 5/1-5/2.
Digiorgio, James, "Is Your Emergency Department of the Leading Edge?", Internet, 2005, pp. 1-4.
Discovery Channel Canada, "Inventing the Future: 2000 Years of Discovery", (Video Transcript), Jan. 2, 2000.
Elhajj, et al., "Supermedia in Internet-based telerobotic operations", Internet, 2001, pp. 1-14.
Elhajj, et al., "Synchronization and Control of Supermedia Transmission Via the Internet", Proceedings of 2001 International Symposium on Intelligent Multimedia Video and Speech Processing., Hong Kong, May 2-4, 2001.
Ellison, et al., "Telerounding and Patient Satisfaction Following Surgery", pp. 523-530.
Fels, "Developing a Video-Mediated Communication System for Hospitalized Children", Telemedicine Journal, vol. 5, vol. 5, No. 2, 1999.
Fetterman, "Videoconferencing over the Internet", Internet, 2001, pp. 1-8.
Ghiasi, et al., "A Generic Web-based Teleoperations Architecture: Details and Experience", SPIE Conference on Telemanipulator and Telepresence Technologies VI, Sep. 1999.
Goldberg, et al., "Collaborative Teleoperation via the Internet", IEEE International Conference on Robotics and Automation, San Francisco, California, Apr. 2000.
Goldberg, "Desktop Teleoperation via the World Wide Web, Proceedings of the IEEE International Conference on Robotics and

(56) References Cited

OTHER PUBLICATIONS

Automation", htto://citeseer.ist.osu.edu/cache/oaoers/cs/5/ fto:zSzzSzusc.eduzSzoubzSziriszSzraiders.odf/aol, 1995, pp. 654-659.

Goldberg, "More Online Robots, Robots that Manipulate", Internet, Updated Aug. 2001, http://ford.ieor.berkeley.edu/ir/robots_a2.html, Aug. 2001.

Goldenberg, et al., "Telemedicine in Otolaryngology", American Journal of Otolaryngology vol. 23, No. 1, 2002, pp. 35-43.

Goldman, Lea, "Machine Dreams", Entrepreneurs, Forbes, May 27, 2002.

Gump, Michael D., "Robot Technology Improves VA Pharmacies", Internet, 2001, pp. 1-3.

Hameed, Mohammed et al., "A Review of Telemedicine", Journal of Telemedicine and Telecare., vol. 5, Supplement 1, 1999, pp. S1:103-S1:106.

Han, et al., "Construction of an Omnidirectional Mobile Robot Platform Based on Active Dual-Wheel Caster Mechanisms and Development of a Control Simulator", Kluwer Acedemic Publishers, vol. 29, Nov. 2000, pp. 257-275.

Handley, et al., "RFC 2327—SDP:Session Description Protocol", http://www.faqs.org/rfcs/rfc2327.html, Apr. 1998.

Hanebeck, et al., "ROMAN: A mobile Robotic Assistant for Indoor Service Applications", Proceedings of the 1997 IEEE/RSJ International Conference on Intelligent Robots and Systems, 1997.

Harmo, et al., "Moving Eye—Interactive Telepresence Over Internet With a Ball Shaped Mobile Robot", 2000.

Haule, et al., "Control Scheme for Delayed Teleoperation Tasks", Proceedings of the Pacific Rim Conference on Communications, Computer and Signal Processing, May 17, 1995.

Hees, William P., "Communications Design for a Remote Presence Robot", Jan. 14, 2002.

Holmberg, "Development of a Holonomic Mobile Robot for Mobile Manipulation Tasks", International Conference on Field and Service Robotics, Pittsburgh, PA, Aug. 1999.

Int'l Communication Union, "ITU-T H.323 Packet-based multimedia communications", http://www.itu.int/rec/T-REC-H.323-199802-S/en, Feb. 1998.

Ishiguro, "Integrating a Perceptual Information Infrastructure with Robotic Avatars: A Framework for Tele-Existence", Proceeding of IEEE Conference on Intelligent Robots and Systems, 1999, pp. 1032-1038.

Ishihara, et al., "Intelligent Microrobot DDS (Drug Delivery System) Measured and Controlled by Ultrasonics", IEEE/RSJ, vol. 2, Nov. 3-5, 1991, pp. 1145-115.

Ivanova, Natal!, "Master's thesis: Internet Based Interface for Control of a Mobile Robot", Department of Numerical Analysis and Computer Science, 2003, 59 pages.

Jenkins, et al., "Telehealth Advancing Nursing Practice", Nursing Outlook, vol. 49, No. 2, Mar./Apr. 2001.

Johanson, "Supporting video-mediated communication over the Internet", Chalmers University of Technology,Dept of Computer Engineering, Gothenburg, Sweden, 2003.

Jouppi, et al., "Mutually-Immersive Audio Telepresence", Audio Engineering Society Convention Paper presented at 113th Convention, Oct. 2002.

Jouppi, Norman et al., "First Steps Towards Mutually-Immersive Mobile Telepresence", CSCW, 02, New Orleans LA, Nov. 16-20, 2002.

Kanehiro, Fumio et al., "Virtual Humanoid Robot Platform to Develop Controllers of Real Humanoid Robots without Porting", IEEE, 2001, pp. 3217-3276.

Kaplan, A. E. et al., "An Internet Accessible Telepresence", {aek keshav nls jhv}@research.att.com, AT&T Bell Laboratories, Murray Hill, N.J., pp. 1-7.

Keller, et al., "Raven Interface Project", http://upclose.lrdc.pitt.edu/people/louw_assets/Raven_Slides.pps, Fall 2001.

Khatib, "Robots in Human Environments", Proc. International Conference on Control, Automation, Robotics, and Vision ICRACV2000, Singapore, Dec. 2000, pp. 454-457.

Kuzuoka, et al., "Can the GestureCam Be a Surrogate?", Proceedings of the Fourth European Conference on Computer-Supported Cooperative Work, Sep. 10-14, pp. 181-196.

Lane, "Automated Aides", Newsday, http://www.cs.cum.edu/nursebot/web/press/nd4380.htm, Oct. 17, 2000.

Lee, et al., "A novel method of surgical instruction: International telementoring", Internet, 1998, pp. 1-4.

Lim, Hun-Ok et al., "Control to Realize Human-like Walking of a Biped Humanoid Robot", IEEE, 2000, pp. 3271-3276.

Linebarger, John M. et al., "Concurrency Control Mechanisms for Closely Coupled Collaboration in Multithreaded Virtual Environments", Presence, Special Issue on Advances in Collaborative VEs, 2004.

Loeb, et al., "Virtual Visit: Improving Communication for Those Who Need It Most", Stud Health Technol Inform.; 94: 2003 pp. 302-308.

Long, "HelpMate Robotics, Inc. (Formerly Transitions Research Corporation) Robot Navigation Technology", NIST Special Publication, http://www.atp.nist.gov/eao/sp950-1/helpmate.htm, Mar. 1999, pp. 950-951.

Luna, Nancy, "Robot a new face on geriatric care", OC Register, Aug. 6, 2003.

Mack, "Minimally invasive and robotic surgery", Internet IEEE, 2001, pp. 568-572.

Mair, "Telepresence—The Technology. And Its Economic and Social Implications", IEEE Technology and Society, 1997.

Martin, Anya, "Days Ahead", Assisted Living Today, vol. 9, Nov./Dec. 2002, pp. 19-22.

McCardle, et al., "The challenge of utilizing new technology in design education", Internet, 2000, pp. 122-127.

Meng, et al., "E-Service Robot in Home Healthcare", Proceedings of the 2000 IEEE/RSJ, International Conference on Intelligent Robots and Systems, 2000, pp. 832-837.

Michaud, "Introducing Nursebot", The Boston Globe, http://www.cs.cmu.edu/nursebot/web/press/globe 3 01/index.html, Sep. 11, 2001, pp. 1-5.

Montemerlo, "Telepresence: Experiments in Next Generation Internet", CMU Robotics Institute, http://www.ri.cmu.edu/creative/archives.htm (Video/Transcript), Oct. 20, 1998.

Murphy, "Introduction to A1 Robotics", A Bradford Book, 2000, p. 487.

Nakajima, et al., "A Multimedia Teleteaching System using an Electronic Whiteboard for Two Way Communication of Motion Videos and Chalkboards", IEEE, 1993, pp. 436-441.

Nomadic Technologies Inc., "Nomad XR4000 Hardware Manual", Release 1.0, Mar. 1999.

Nt'l Energy Res Sci Comp Ctr, "Berkeley Lab's RAGE Telepresence Robot Captures R&D100 Award", http://www.nersc.gov/news/newsroom/RAGE070202.php, Jul. 2, 2002,.

Ogata, et al., "Development of Emotional Communication Robot: WAMOEBA-2r- Experimental evaluation .", IEEE, 2000, pp. 175-180.

Ogata, et al., "Emotional Communication Robot: WAMOEBA-2R-Emotion Model and Evaluation Experiments", Internet, 1999, pp. 1-16.

Oh, et al., "Autonomous Battery Recharging for Indoor Mobile Robots", Proceedings of Australian Conference on Robotics and Automation, http://users.rsise.anu.edu.au/rsl/rsl_papers/ACRA2000/Auto_Recharge_Paper.pdf, 2000.

Ojha, A. K., "An application of Virtual Reality in Rehabilitation", IEEE, Apr. 10-13, 1994, pp. 4-6.

Paulos, et al., "A World Wide Web Telerobotic Remote Environment Browser", http://vive.cs.berkeley.edu/capek, 1995.

Paulos, "Designing Personal Tele-embodiment", IEEE International Conference on Robotics and Automation http://www.prop.org/papers/icra98.pdf, 1998.

Paulos, "PRoP: Personal Roving Presence", ACM:CHI Proceedings of CHI '98, http://www.prop.org/papers/chi98.pdf, 1998, p. 6.

Paulos, et al., "Ubiquitous Tele-embodiment: Applications and Implications", International Journal of Human Computer Studies, vol. 46, No. 6, Jun. 1997, pp. 861-877.

(56) References Cited

OTHER PUBLICATIONS

Paulos, "Video of PRoP 2 at Richmond Field Station", www.prop.org Printout of Home Page of Website and two-page Transcript of the audio portion of said PRoP Video, May 2001.
Paulos, Eric J., "Personal Tele-Embodiment", UC Berkeley, Fall 2001.
Pin, et al., "A New Family of Omnidirectional and Holonomic Wheeled Platforms for Mobile Robots", IEEE, vol. 10, No. 4, Aug. 1994.
Rovetta, et al., "A New Telerobotic Application: Remote Laparoscopic Surgery Using Satellites and and optical fiber Networks for Data Exchange", International Journal of Robotics Research, Jun. 1, 1996, pp. 267-279.
Roy, et al., "Towards Personal Service Robots for the Elderly", Internet, Mar. 7, 2002, 7 pgs.
Salemi, et al., "MILO: Personal robot platform", Internet, 2005, pp. 1-6.
Sandt, Frederic et al., "Perceptions for a Transport Robot in Public Environments", IROS, 1997.
Schaeffer, "Care-O-bot: A System for Assisting Elderly or Disabled Persons in Home Environments", Proceedings of AAATE-99, http://morpha.de/download/publications/IPA, 1999.
Schulz, "Web Interfaces for Mobile Robots in Public Places", Robotics & Automation Magazine, IEEE, vol. 7, Issue 1, Mar. 2000.
Shimoga, et al., "Touch and force reflection for telepresence surgery", IEEE, 1994, pp. 1049-1050.
Siegwart, "Interacting Mobile Robots on the Web", Proceedings of the 1999 IEEE International Conference on Robotics and Automation, May 1999.
Simmons, "Xavier: An Autonomous Mobile Robot on the Web", IEEE Robotics and Automation Magazine, 1999, pp. 43-48.
Spawar Systems Center, "Robart", San Diego, CA, http://www.nosc.mil/robots/land/robart/robart.html, 1998, pp. 1-8.
Stephenson, Gary, "Dr. Robot Tested at Hopkins", Internet, Aug. 5, 2003, pp. 1-2.
Stoianovici, et al., "Robotic Tools for Minimally Invasive Urologic Surgery", Internet, Dec. 2002, pp. 1-17.
Suplee, , "Mastering the Robot", The Washington Post, http://www.cs.cmu.edu-nursebotlweb/press/wash/index.html, Sep. 17, 2000, p. A01.
Tahboub, Karim A. et al., "Dynamics Analysis and Control of a Holonomic Vehicle With Continously Variable Transmission", Journal of Dynamic Systems, Measurement and Control ASME vol. 124, Mar. 2002, pp. 118-126.
Tendick, et al., "Human-Machine Interfaces for Minimally Invasive Surgery", IEEE, 1997, pp. 2771-2776.
Thrun, et al., "Probabilistic Algorithms and the Interactive Museum Tour-Guide Robot Minerva", Internet, 2000, pp. 1-35.
Tzafestas, et al., "VR-based Teleoperation of a Mobile Robotic Assistant: Progress Report", Internet, Nov. 2000, pp. 1-23.
Urquhart, Kim , "InTouch's robotic Companion 'beams up' healthcare experts", Medical Device Daily, vol. 7, No. 39, Feb. 27, 2003, p. 1,4.
Weiss, et al., "Telework and video-mediated communication: Importance of real-time, interactive communication for workers with disabilities", California State University Northridge http://www.csun.edu/cod/conf/1999/proceedings/session0238.html, pp. 1-4.
West, et al., "Design of Ball Wheel Mechanisms for Omnidirectional Vehicles with Full Mobility and Invariant Kinematics", Journal of Mechanical Design , vol. 119, Jun. 1997, pp. 153-161.
Yamasaki, et al., "Applying Personal Robots and Active Interface to Video Conference Systems", Internet, 1995, pp. 243-248.
Yamauchi, "PackBot: A Versatile Platform for Military Robotics", Internet, 2004, pp. 1-10.
Yong, et al., "Robot task execution with telepresence using virtual reality technology", Internet, 1998, pp. 1-8.
Zamrazil, Kristie, "Telemedicine in Texas: Public Policy Concerns", House Research Organization Focus Report, Texas House of Representatives, http://www.hro.house.state.tx.us/focus/telemed.pdf, May 5, 2000, pp. 76-22.
Zipperer, Lorri, "Robotic dispensing system", 1999, pp. 1-2.
Zorn, Benjamin G., "Ubiquitous Telepresence", http://www.cs.colorado.edu/-zorn/utlvision/vision.html, May 5, 1996.
Barrett, "Video Conferencing Business Soars as Companies Cut Travel; Some Travel Cuts Are Permanent", http://www.ivci.com/international_videoconferencing_news_videoconferencing_news_19.html, Mar. 13, 2002.
Brooks, "A Robust Layered Control System for a Mobile Robot," IEEE Journal of Robotics and Automation, 2 (1), Mar. 1986, 10 pgs.
Davis, "Meet iRobot, The Smartest Webcam on Wheels," Wired Magazine, 8.09, http://www.wired.com/wired/archive/8.09/irobot_pr.html, Sep. 2000, 2 pgs.
Dean, et al., "1992 AAAI Robot Exhibition and Competition," AI Magazine, Spring 1993, 10 pgs.
"Defendant VGo Communications, Inc.'s Invalidity Contentions Pursuant to the Feb. 27, 2012 Civil Minute Order", May 2, 2012.
"Defendant-Counterclaimant VGo Communications, Inc.'s Supplemental Invalidity Contentions Pursuant to the Feb. 27, 2012 Civil Minute Order", May 14, 2012.
Dudenhoeffer, et al., "Command and Control Architectures for Autonomous Micro-Robotic Forces", http://www.inl.gov/technicalpublications/Documents/3157051.pdf, Apr. 2001.
Elhajj, "Real-Time Haptic Feedback in Internet-Based Telerobotic Operation", IEEE International Conference on Electro/Information Technology, http://www.egr.msu.edu/~ralab-web/cgi_bin/intemet-teleoperation.php, Jun. 2000.
Fiorini, et al., "Health Care Robotics: A Progress Report", IEEE International Conference on Robotics and Automation, 1997., Apr. 1997, pp. 1271-1276.
Fong, "Collaborative Control: A Robot-Centric Model for Vehicle Teleoperation", The Robotics Institute Carnegie Mellon University, http://web.archive.org/web/20030504040803/www.ricmu.edu/cgi-bin/tech_reports.cgi?year=2001&text=0, Nov. 2001.
Grow, "Office Coworker Robot," Time Magazine, http://www.time.com/time/specials/packages/article/0,28804,1936165_1936255_1936640,00.html, Nov. 19, 2001, 2 pgs.
ITU, "ITU-T H.281 A Far End Camera Control Protocol for Videoconferences using H.224", http://www.itu.int/rec/T-RECH.281-199411-I/en, Nov. 1994.
ITU, "ITU-T H.323 Packet-based multimedia communications", http://www.itu.int/rec/T-REC-H.323-199802-S/en, Feb. 1998.
ITU, "ITU-T H.450.11 Call Intrusion Supplementary Service for H.323", http://www.itu.int/rec/T-RECH.450.11-200103-I/en, Mar. 2001.
ITU, "ITU-T H.450.9 Call Completion Supplementary Services for H.323", http://www.itu.int/rec/T-RECH.450.9-200011-I/en, Nov. 2000.
Knight, et al., "Active Visual Alignment of a Mobile Stereo Camera Platform", Proceedings of the IEEE, International Conference on Robotics and Automation, San Francisco, Apr. 24-28, 2000, pp. 3202-3208.
Metz, "HP Labs", PCMAG.com, http://www.pcmag.com/article2/0,2817,1130820,00.asp, Jul. 1, 2003.
PictureTel, "PictureTel Live200 for Windows NT Product Guide", http://support.polycom.com/global/documents/support/user/products/video/live200_live200NT_product_guide.pdf, Nov. 1994.
"PictureTel Adds New Features and Functionality to Its Award-Winning Live200 Desktop Videoconferencing System", PR Newswire Association, LLC, Gale, Cengage Learning, http://www.thefreelibrary.com/PictureTel+Adds+New+Features+And+Functionality+To+Its+Award-Winning...-a019512804, Jun. 13, 1997.
Roach, "Automatic Call Back Service in SIP", http://tools.ieff.org/pdf/draftroach-sip-acb-00.pdf, Mar. 2000.
Summers, "Microsoft NetMeeting 3 Features excerpt from Official Microsoft NetMeeting 3.0 Book", http://technet.microsoft.com/en-us/library/cc723477.aspx#XSLTsection121121120120, excerpt from Microsoft Press http://www.computerbooksonline.com/abook.asp?i=0735605823, Mar. 1999.
U.S. Appl. No. 10/783,760, filed Feb. 20, 2004, Wang, et al., 48 pgs.
U.S. Appl. No. 60/449,762, filed Feb. 24, 2003, Wang, et al., 28 pgs.

(56) References Cited

OTHER PUBLICATIONS

Weiss, et al., "PEBBLES: A Personal Technology for Meeting Education, Social and Emotional Needs of Hospitalised Children", Personal and Ubiquitous Computing 5, Springer-Verlag London Ltd., 2001, pp. 157-168.
Zambroski, "CMU, Pitt Developing 'nursebot'", http://www.cs.cmu.edu/~nursebot/web/press/tribunereview.html, Oct. 27, 2000.
Appeal from the U.S. District Court for the Central District of California in case No. 11-cv-9185, Judge Percy Anderson, Joint Appendix, vol. I of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Civil Minutes—General: Case No. CV 11-9185PA (AJWx), *InTouch Tech., Inc.* v. *VGo Commons, Inc.*, U.S. District Court for the Central District of California, Judge Percy Anderson, Sep. 10, 2012, 7 pages.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.
Office Action received for Chinese Patent Application No. 200680044698.0 on Nov. 4, 2010. (9 pages of Official Copy and 17 pages of English Translation).
"Magne Charge", Smart Power for Electric Vehicles, General Motors Corporation, Serial No. 75189637, Registration No. 2114006, Filing Date: Oct. 29, 1996, Aug. 26, 1997, 2 pages.
Activmedia Robotics LLC, "Pioneer 2/PeopleBot™", Operations Manual, Version 9, Oct. 2001, 78 pages.
Active Media, Inc., "Saphira Software Manual", Real World, Saphira Version 5.3, 1997, 105 pages.
Apple Inc., "I Phone", iPhone Series, XP002696350, Sep. 21, 2012, pp. 1-29.
Blaer et al., "TopBot: Automated Network Topology Detection With a Mobile Robot", IEEE, Proceedings of the 2003 International Conference on Robotics and Automation, Taipei, Taiwan, Sep. 14-19, 2003, pp. 1582-1587.
Bradner, S., "The Internet Standards Process—Revision 3", Network Working Group, Request for Comments: 2026, BCP: 9, Obsoletes: 1602, Category: Best Current Practice, Oct. 1996, pp. 1-36.
Christensen et al., "BeeSoft User's Guide and Reference", Robots for the Real World™, Real World Interface, Inc ., Sep. 26, 1997, 203 pages.
Chu et al., "Detection of Target Mobile Signal Strength", Technical Development, Motorola Inc., Jan. 1999, pp. 205-206.
Dario et al., "A Robot Workstation for Diagnosis and Physical Therapy", IEEE Catalog No. 88TH0234-5, Centro "E. Piaggio" University of Pisa, Italy, 1989, pp. 67-72.
Evans et al., "HelpMate: The Trackless Robotic Courier", PYXIS, available online at <http://www.pyxis.com/>, 3 pages.
Adams, Chris, "Simulation of Adaptive Behavior (SAB'02)—From Animals to Animats 7", Mobile Robotics Research Group, The Seventh International Conference, available online at: <http://www.dai.ed.ac.uk/groups/mrg/MRG.html>, retrieved on Jan. 22, 2014, Aug. 4-11, 2002, 1 page.

Garner et al., "The Application of Telepresence in Medicine", BT Technology Journal, vol. 15, No. 4, Oct. 1, 1997, pp. 181-187.
Gostai "Gostai Jazz: Robotic Telepresence", available online at <http://www.gostai.com>, 4 pages.
Jacobs et al., "Applying Telemedicine to Outpatient Physical Therapy", AMIA, Annual Symposium Proceedings, 2002, 1 page.
Kurlowicz et al., "The Mini Mental State Examination (MMSE)", The Hartford Institute for Geriatric Nursing, Journal of Psychiatric Research, No. 3, Jan. 1999, 2 pages.
Leifer et al., "VIPRR: A Virtually in Person Rehabilitation Robot", Proceedings of 1997 International Conference on Rehabilitation Robotics, Apr. 14-15, 1997, 4 pages.
Lemaire, Edward, "Using Communication Technology to Enhance Rehabilitation Services", Terry Fox Mobile Clinic, The Rehabilitation Centre, Ottawa, Canada, Version 2.0, 1998-2001, 104 pages.
Minsky, Marvin, "Telepresence", OMNI Magazine, Jun. 1980, 6 pages.
Nakazato et al., "Group-Based Interface for Content-Based Image Retrieval", Proceedings of the Working Conference on Advanced Visual Interfaces, 2002, pp. 187-194.
Nakazato et al., "Group-Oriented User Interface for Digital Image Management", Journal of Visual Languages and Computing, vol. 14, No. 4, Aug. 2003, pp. 45-46.
Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.
North, Michael, "Telemedicine: Sample Script and Specifications for a Demonstration of Simple Medical Diagnosis and Treatment Using Live Two-Way Video on a Computer Network", Greenstar Corporation, 1998, 5 pages.
Osborn et al., "Quality of Life Technology Center", QoLT Research Overview: A National Science Foundation Engineering Research Center, Carnegie Mellon University of Pittsburgh, 2 pages.
Piquepaille, Roland, "How New Technologies are Modifying Our Way of Life", Roland Piquepaille's Technology Trends, This Blog and its RSS Feed Are Moving, Oct. 31, 2004, 2 pages.
"Using your Infrared Cell Phone Camera", Available on <http://www.catsdomain.com/xray/about.htm>, retrieved on Jan. 23, 2014, Courtesy of Internet Wayback Machine, Jan. 30, 2010, 4 pages.
Reynolds et al., "Review of Robotic Telemedicine Utilization in Intensive Care Units (ICUs)", 11th Annual ATA Symposium, Tampa, Florida, 2011, 1 page.
Roy et al., "Towards Personal Service Robots for the Elderly", Workshop on Interactive Robots and Entertainment (WIRE 2000), vol. 25, Apr. 30-May 1, 2000, 7 pages.
Telepresence Research, Inc., "Telepresence Mobile Robot System", available online at <http://www.telepresence.com/telepresence-research/TELEROBOT/>, retrieved on Nov. 23, 2010, Feb. 20, 1995, 3 pages.
Theodosiou et al., "MuLVAT: A Video Annotation Tool Based on XML-Dictionaries and Shot Clustering", 19th International Conference, Artificial Neural Networks—ICANN, Sep. 14-17, 2009, pp. 913-922.
Tipsuwan et al., "Gain Adaptation of Networked Mobile Robot to Compensate QoS Deterioration", vol. 4, 28th Annual Conference of the Industrial Electronics Society, Nov. 5-8, 2002, pp. 3146-3151.
Tsui et al., "Exploring Use Cases for Telepresence Robots", 6th ACM/IEEE International Conference on Human-Robot Interaction (HRI), Mar. 2011, 7 pages.
Tyrrell et al., "Teleconsultation in Psychology: The Use of Videolinks for Interviewing and Assessing Elderly Patients", British Geriatrics Society, Age and Ageing, vol. 30, No. 3, May 2001, pp. 191-195.
UMASS Lowell Robotics Lab, "Robotics Lab @ UMASS Lowell", Department of Computer Science, Brochure, 2011, 2 pages.
Video Middleware Cookbook, "H.350 Directory Services for Multimedia", 4 pages.
Weaver et al., "Monitoring and Controling Using the Internet and Java", Proceedings of the 25th Annual Conference of the IEEE Industrial Electronics Society, vol. 3, 1999, pp. 1152-1158.

* cited by examiner

SYSTEMS AND METHODS FOR DYNAMIC BANDWIDTH ALLOCATION

DETAILED DESCRIPTION OF PREFERRED EMBODIMENTS

Figure 1:
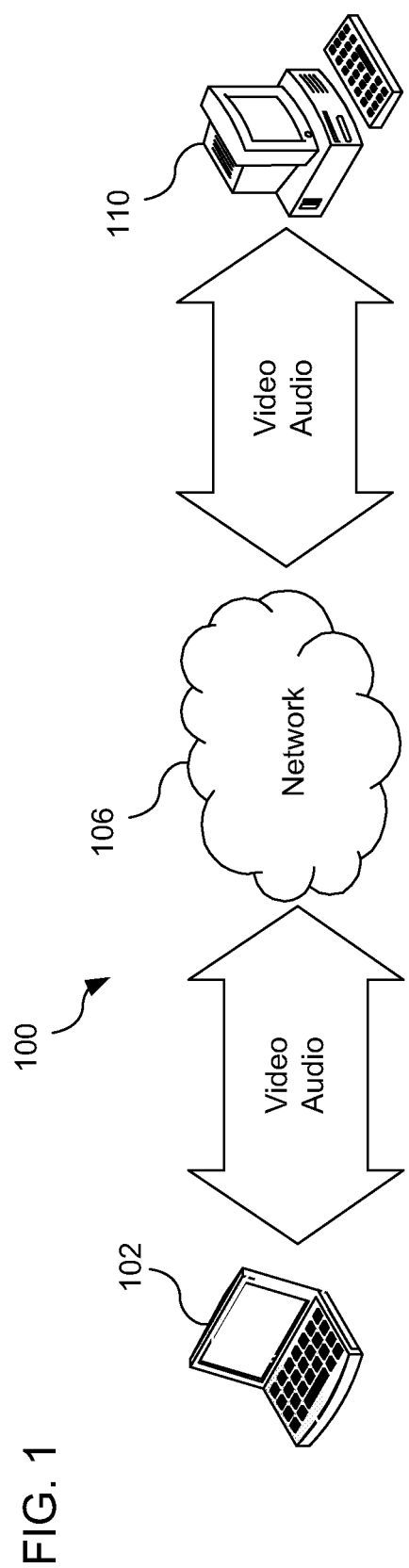
FIG. 1 illustrates a functional block diagram of one embodiment of a videoconferencing system, which may utilize various techniques for dynamically adjusting bandwidth utilization between two endpoints.

Disclosed herein are various embodiments of systems and methods that may be utilized in a variety of videoconferencing applications. According to various embodiments, techniques may be utilized to dynamically allocate and adjust bandwidth utilization during a videoconferencing session.

A data network may allow for the transmission of data between two or more endpoints. The data exchanged between the endpoints may include video data, audio data, control data, and status data. Control data may be utilized in various embodiments to operate a robotic videoconferencing endpoint. Accordingly, various components of a data network connecting videoconferencing endpoints may transmit data wirelessly. Status data may refer to any type of data that is not video data, audio data, or control data.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. In particular, an "embodiment" may be a system, an article of manufacture (such as a computer readable storage medium), a method, and a product of a process.

The phrases "connected to," and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless specified to require an order.

Embodiments may include various features, which may be embodied in machine-executable instructions executed by a general-purpose or special-purpose computer (or other electronic device). Alternatively, the features may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

FIG. 1 illustrates a diagram of one embodiment of a videoconferencing system 100, which may utilize various techniques disclosed herein for dynamically adjusting bandwidth utilization between two endpoints 102 and 110. Endpoint 102 is in communication with endpoint 110 via network 106. Each of endpoints 102 and 110 generate audio and video data, which is transmitted via network 106. Each of endpoints 102 and 110 also receive audio and video data. The audio and video data received by each of endpoints 102 and 110 may allow users of the respective endpoints to communicate visually and audibly.

Data network 106 represents any type of data network that may facilitate data communication between endpoints 102 and 110. For example, network 106 may comprise a local area network or a wide area network. Network 106 may comprise an intranet, a virtual private network, or a public network, such as the Internet or other data communications networks (e.g., cellular data networks). Network 106 may further comprise routers, gateways, firewalls, wireless network adapters, and other types of networking equipment.

Various types of endpoints are contemplated, including fixed and mobile videoconferencing endpoints. In embodiments having one or more mobile endpoints, various wireless technologies may be utilized in order to allow the mobile endpoint to remain in data communication with network 106. Various embodiments disclosed herein may be utilized in connection with robotic systems employed for a variety of applications. One such embodiment is illustrated in FIG. 2.

Figure 2:
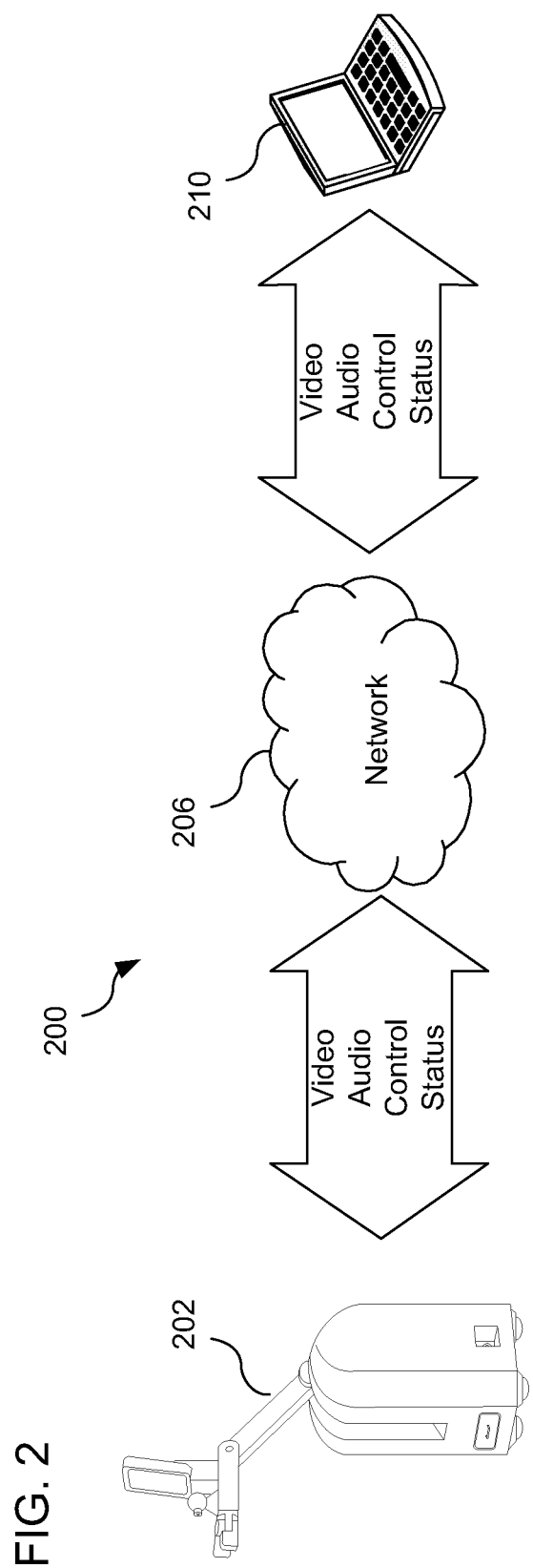
FIG. 2 illustrates a functional block diagram of one embodiment of a system, which may utilize various techniques for dynamically adjusting bandwidth utilization between two endpoints.
Figure 3:
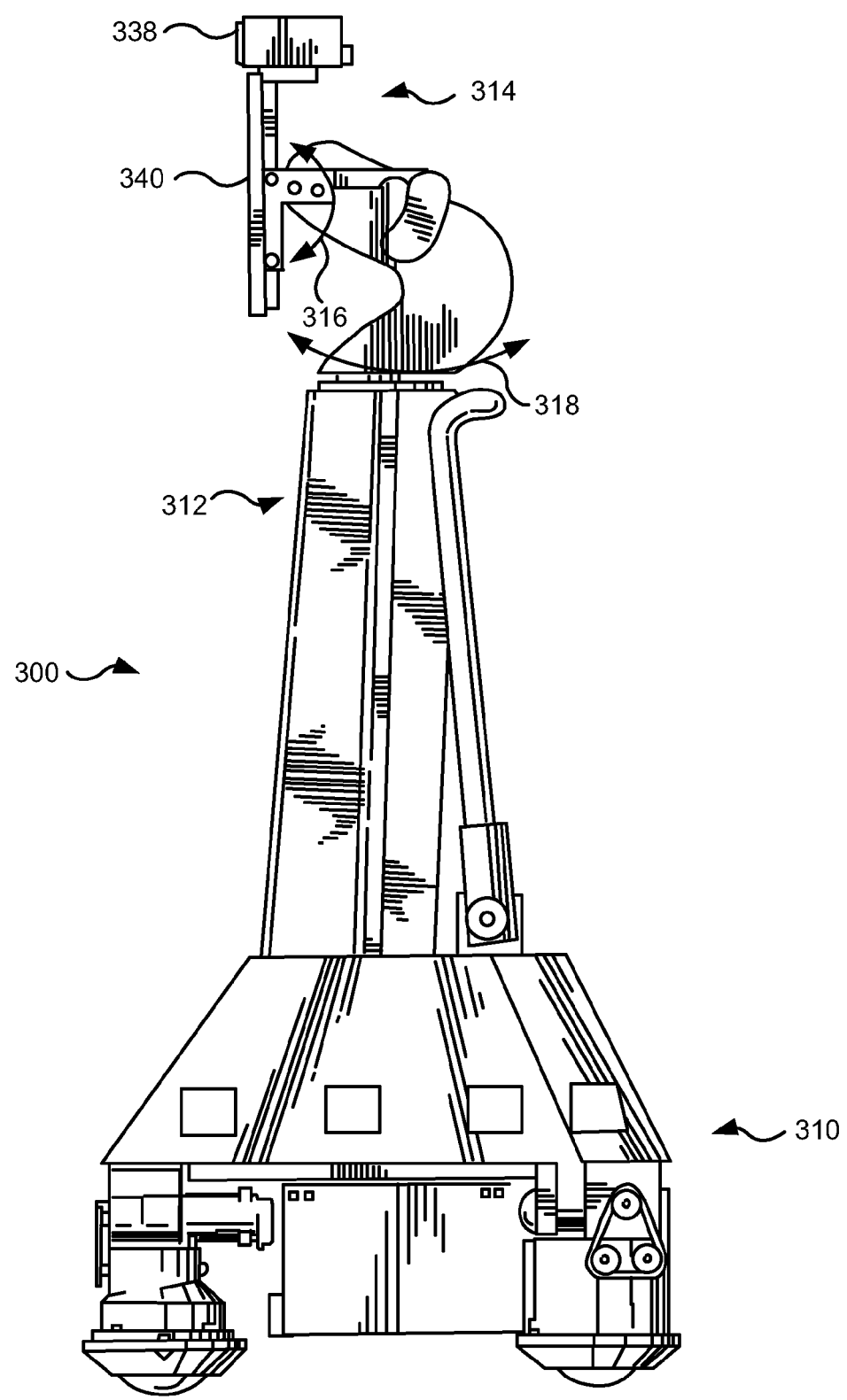
FIG. 3 illustrates a perspective view of one embodiment of a robotic videoconferencing endpoint.

FIG. 2 illustrates a functional block diagram of a system 200, which may utilize various techniques disclosed herein for dynamically adjusting bandwidth utilization between two endpoints. An endpoint 202, which is illustrated and described in greater detail in connection with FIG. 3, is in communication with an endpoint 210 via a data network 206. Each of endpoints 202 and 210 may comprise suitable network adapters to enable transmission to, and receipt of data from, data network 206.

Endpoints 202 and 210 exchange a variety of types of data, including video data, audio data, control data, and status data via data network 206. Data network 206 represents any type of data network that may facilitate data communication between endpoints 202 and 210. For example, network 206 may comprise a local area network or a wide area network. Network 206 may comprise an intranet, a virtual private network, or a public network, such as the Internet or other data communications networks (e.g., cellular data networks). Network 206 may further comprise routers, gateways, firewalls, wireless network adapters, and other types of networking equipment.

System 200 may be employed, for example, by a medical practitioner or other care provider to monitor individuals at a remote location. According to various embodiments, data prioritization schemes may be employed so that higher priority data is transmitted with greater reliability or at a higher data rate than lower priority data. For example, in system 200 control data transmitted from second endpoint 210 to first endpoint 202 may be designated as high priority data. Such a prioritization may allow a user to remain in control of the motion of endpoint 202, even if network throughput is reduced. Status data, which may include telemetry data gathered from a patient (e.g., pulse rate, EKG, oxygenation, etc.), may also be designated as relatively high priority data. Audio data may be prioritized before video data, such that a medical practitioner and patient can maintain audible communication. Finally, video data may be transmitted using the lowest priority. According to various embodiments, audio data and video data variable compression schemes may be utilized in order to more efficiently utilize available bandwidth. During periods of decreased network throughput, a higher compression ratio may be utilized for video and/or audio data. Such compression may reduce the quality of the video and/or audio data; however, such compression may allow for continued use of system 200 even if data throughput is reduced. In still other embodiments, a video frame rate may be adjusted dynamically, prior to segmenting the data into packets. According to various embodiments, status data comprising information gathered from patient sensors (e.g. an EKG sensor, a blood oxygenation sensor, etc.) may receive the highest priority.

The data transmitted between endpoints 202 and 210 may be asymmetrical in quantity and/or priority. For example, in telemedicine applications, data flowing from the remote station to the robot is less critical than video and data flowing from endpoint 202 to endpoint 210. Various embodiments of system 200 may allow dynamic adjustment of bandwidth, such that the minimum allowable bandwidth from one endpoint is higher than the minimum allowable bandwidth from the other endpoint. For example, the allowable outgoing data rate from endpoint 210 may be in the range of 150 kbps to 700 kbps, but the allowable outgoing data rate from endpoint 202 may be in the range of 200 kbps to 700 kbps. For example, a data rate of less than 200 kbps may make diagnosis problematic and impede the ability to drive a robotic videoconferencing endpoint.

According to various embodiments, data may be prioritized at the application layer. According to such embodiments, the application generating video and audio and control/sensor data may be aware of the available bandwidth and may adjust the content to be transmitted accordingly. Such an application may allow for a user to customize settings to be used during a particular session or at various points within a session. For example, in one embodiment where an endpoint is used in telemedicine applications, the quality images received from an endpoint near a patient may be assigned a higher priority, depending on whether a diagnosis is made using the images. For example, if a dermatologist is utilizing a videoconferencing endpoint to obtain images of a rash on a patient's skin, image quality may be assigned a greater importance than other characteristics (e.g., a video frame rate). In another example, a physician counselling with the patient may not be relying on images to provide a diagnosis. In this example, audio data may receive a high priority, so that audio communications between the patient and physician are maintained even if network throughput declines. In still another example, during a videoconferencing session a physician may drive a robotic videoconferencing endpoint from one location in a medical facility to another location. While the videoconferencing endpoint is in motion, frame rate may be assigned a higher priority than image quality, such that a remote driver is better able to control the movement of the robotic videoconferencing endpoint. According to various embodiments, a robotic videoconferencing endpoint may be configured such that upon detection of base motion, prioritization switches from image quality to frame rate.

FIG. 3 illustrates a perspective view of one embodiment of a robotic videoconferencing endpoint 300. Videoconferencing endpoint 300 may include a robotic platform 310 that is attached to a robot housing 312. Robotic platform 310 may allow videoconferencing endpoint 300 to move in any direction. Videoconferencing endpoint 300 may include a robotic head 314 that supports a video camera 338 and a monitor 340. Robotic head 314 may allow a user to pan and tilt the video camera 338 and monitor 340 using pan and tilt actuators, as indicated by arrows 316 and 318. Robotic head 314, and robotic platform 310 may be referred to individually as robotic elements. Each of robotic head 314, and robotic platform 310 may operate in conjunction with a robotic driver that is configured to receive and implement instructions for controlling the various robotic elements.

Figure 4:
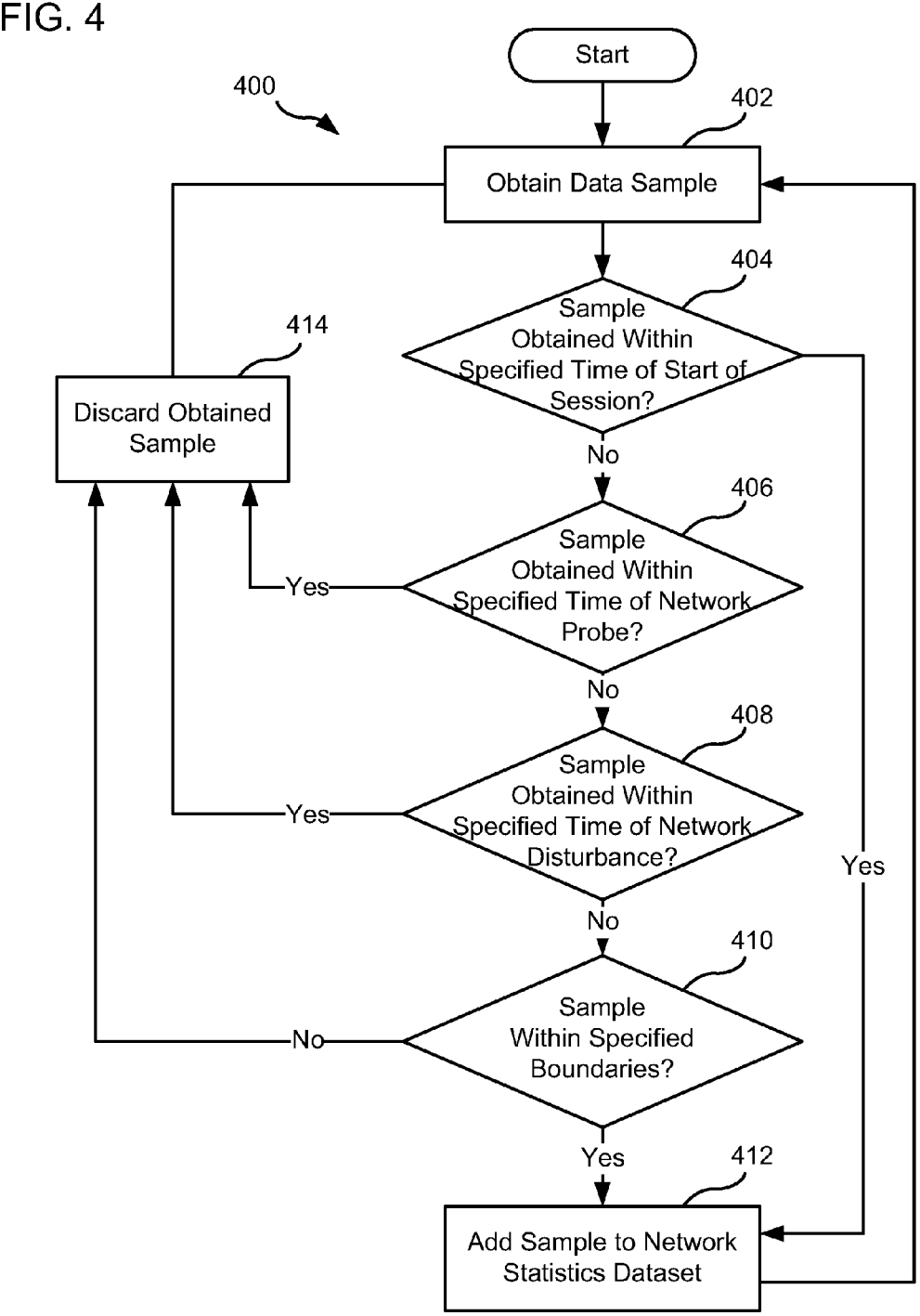
FIG. 4 illustrates one embodiment of a method of monitoring network statistics in a videoconferencing session and for determining which data samples are added to the network statistics dataset during a videoconferencing session.

FIG. 4 illustrates one embodiment of a method 400 for monitoring network statistics in a videoconferencing session and for determining which data samples are added to the network statistics dataset. The network statistics dataset may comprise a plurality of data samples that represent one or more quantifiable metrics of network conditions. Method 400 may be utilized during the entirety of a videoconferencing session between two or more videoconferencing endpoints. Accordingly, a network statistics dataset may be continually updated during a videoconference, and up-to-date information regarding network conditions may be utilized in connection with dynamic bandwidth allocation. According to various embodiments, such metrics may include, but are not limited to, measurements of latency, average data throughput, variations in latency over time, and the like. According to various embodiments, the network statistics dataset may include samples from the initiation of a videoconference, or only a trailing number of samples or minutes of samples.

A network statistics dataset may be established at the initiation of a session. In certain embodiments, an initial network statistics dataset may be created during an initial period in which data transmission occurs at a baseline rate. The baseline rate may be relatively minor in comparison to the theoretical throughput of the network connection between the endpoints. For example, a baseline rate in one embodiment may be established at the minimum allowable bandwidth for the endpoint, for example 150 kbps for outgoing data from endpoint 210 and 200 kbps for outgoing data from endpoint 202. The minimum allowable bandwidth has the highest probability of being stable for a given network connection. Such embodiments may allow for the creation of a robust network statistics dataset when the network connection between two or more endpoints is operating substantially below its theoretical throughput.

At 402, a data sample is obtained that represents at least one measurement of then-current network conditions. As discussed above, a data sample may, for example, comprise a measurement of latency, average data throughput, etc. In the present example, the measurement utilized is the latency associated with a ping; however, in other embodiments, similar principles may be utilized and adapted for analysis of other types of data samples. Method 400 determines at 404 whether the sample was obtained within a specified time of the start of a session. As discussed above, a network statistics dataset may be established at the initiation of the session during a period when the baseline transmission rate is significantly lower than the theoretical throughput of the network connection between the endpoints. Accordingly, if the data sample was obtained within the specified time of the start of a videoconferencing session, method 400 may proceed to determine whether the sample is within specified boundaries 410, as discussed in greater detail below.

After the passage of a specified amount time from the start of a session, method 400 may determine whether the sample was obtained within a specified time of a network probe 406. As the term is utilized herein, a network probe refers to an increase of bandwidth utilized by one or more endpoints participating in a videoconferencing session. The network probe may temporarily disturb a metric quantified by the obtained data sample, and accordingly, a sample obtained within a specified period following the network probe may be indicative of only a transitory state. According to various embodiments, a specified time may be established following a network probe during which data samples are discarded, so as to reduce the effects of such transitory samples on the network statistics dataset. If the data sample was obtained within the specified time of the network probe, the obtained sample may be discarded 414.

At 408, it may be determined whether the obtained data sample is within a specified time of a network disturbance. As the term is used herein, a network disturbance is in any event or circumstance, or combinations of events or circumstances, that temporarily affect a quantifiable metric representing network conditions. A network disturbance may include, for example, a disruption in data transmission, increased latency, increased bandwidth utilization by other users, etc. Following a network disturbance, the metric quantified by the obtained data sample may be indicative of only a transitory state. According to various embodiments, a specified time may be established following a network disturbance during which data samples are discarded, so as to reduce the effects of such transitory samples on the network statistics dataset.

At 410, the obtained data sample may be compared to specified boundaries relating to the network statistics dataset. For example, even under stable conditions, the latency of a plurality of data samples may differ significantly. In order to reduce the effect of aberrant data samples, certain criteria may be specified by a user or based on the data in the network statistics dataset. In one example, specified boundaries may exclude obtained data samples above the 90th percentile. Other boundaries may also be utilized. Further, other embodiments may utilize ranges in place of percentile boundaries.

Obtained data samples that are not discarded may then be added to the network statistics dataset at 412. Various criteria may be utilized (e.g., various time periods following the start of a session, a network probe, a network disturbance) to exclude certain obtained data samples from the network statistics dataset. Various criteria may be designed to minimize the influence of transitory conditions and other conditions which may not provide an accurate indication of the operation of the network system. According to one embodiment, the criteria may be specified so that approximately 90% of the obtained data samples included in the network statistics dataset are obtained during periods of relative stability on the network.

A network statistics dataset may be utilized by a videoconferencing system as an estimate of the available bandwidth of a particular network. Various thresholds may be established based upon the network statistics dataset, and one or more data values may be compared to the thresholds in order to determine whether a particular videoconferencing session is utilizing too much bandwidth or utilizing too little bandwidth. Latency may be utilized as one indicator of the condition of the network. According to one embodiment, bandwidth utilization of a videoconferencing system may be reduced when latency exceeds a specified threshold. For example, a system could reduce bandwidth usage whenever a latency measurement exceeds 350 milliseconds; however, a stable and high bandwidth connection may exceed 350 milliseconds ping time, and may result in a situation where the network connection is underutilized. According to other embodiments, a system dynamically managing bandwidth of a videoconferencing session may analyze a particular latency measurement with respect to percentile thresholds.

A network statistics dataset may be used to distinguish high latency and high bandwidth networks from networks exhibiting high latency because of network congestion. As described above, a network statistics dataset may include a plurality of the measurements. For example, a network statistics dataset may comprise a plurality of measurements of latency in a particular network. Analysis of the network statistics dataset may show latency measurements ranging from 100 milliseconds to 300 milliseconds, but 90% of latency measurements in the network statistics dataset are less than or equal to 115 milliseconds. Accordingly, 115 milliseconds may be established as a threshold value. Measurements exceeding 115 milliseconds may indicate network congestion, and may provide an indication of decreasing available bandwidth. According to other embodiments, a fixed offset may also be employed in order to avoid excluding data samples that only slightly exceed the threshold value. For example, a fixed offset of 30 milliseconds may be adopted. In embodiments utilizing a fixed offset, a network disturbance may not be recorded unless one or more data samples indicate a latency greater than the sum of the fixed offset and the threshold value. Embodiments including a fixed offset may provide greater tolerance for variation in latency, while reducing the risk of a false positive in identifying a network disturbance.

In a different example, latency measurements might range from 300 milliseconds to 420 milliseconds, with 90% of the latency measurements less than or equal to 330 milliseconds. In that example, a network disturbance would be detected when latency rises above 330 milliseconds. In this way, a system for dynamically allocating bandwidth adapts to stable high-latency connections.

Figure 5A:
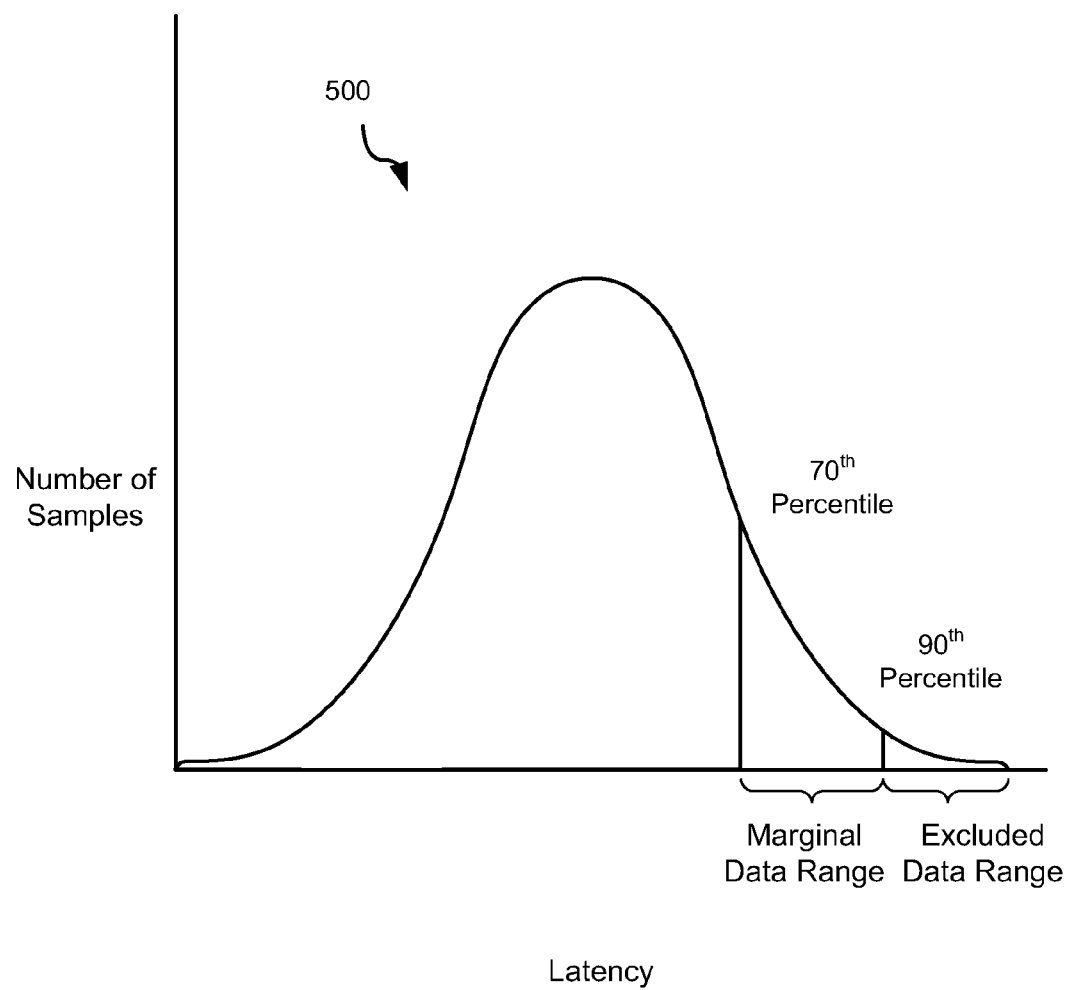
FIG. 5A illustrates an exemplary distribution comprising a plurality of data samples and specified boundaries that may be used in processing newly obtained data samples.

As discussed above, an obtained data sample may be compared against specified boundaries in order to determine whether the obtained data sample should be included in a network statistics dataset. FIG. 5A illustrates an exemplary distribution 500 comprising a plurality of obtained data samples and specified boundaries that may be used in connection with various embodiments. In FIG. 5, the 70th and 90th percentiles of a normal distribution are shown. Depending upon where a particular measurement falls within distribution 500, a system may take various actions. For example, a data sample above the 90th percentile or some other specified percentile may be discarded. Discarding such samples may help to mitigate the effects of statistically aberrant obtained data samples. Data samples falling within these ranges may be referred to as excluded data samples.

Data samples falling between the 70th percentile and 90th percentile may not be immediately discarded, but such samples may not be immediately added to a network statistics dataset. Data samples falling within these ranges may be referred to as marginal data samples. Criteria may be specified in order to determine whether marginal data samples are discarded or added to a network statistics dataset. Various criteria may be associated with the evaluation of marginal data samples. For example, various embodiments may analyze a specified number of subsequently obtained data samples, or may analyze data samples obtained within a specified time (e.g., 60 seconds) before and/or after one or more marginal data samples is obtained.

According to one embodiment, specific criteria for evaluating marginal data samples may be based upon the results of subsequently obtained data samples. For example, a system may experience an increased latency of 100 ms, which arises over a period of 30 seconds. Without a sharp spike in latency, a network disturbance (e.g., the source of the additional latency) may not be recognized, and data samples representing the increased latency may be added to the network statistics dataset. If one or more subsequently obtained data samples within a specified period exceeds a specified threshold (e.g., the 90th percentile) the marginal data samples may be discarded. Subsequent data samples exceeding the specified threshold may indicate that the network is in an unstable condition, and that the marginal data samples do not reflect normal network conditions. If one or more subsequently obtained data samples within a specified period is below a specified threshold (e.g., the 70th percentile), the marginal data samples may be added to the network statistics dataset. Such a data sample may indicate that the marginal data samples reflect normal network conditions. Finally, if one or more subsequently obtained data samples within a specified period is between the 70th percentile and the 90th percentile, the marginal data samples may be included in the network statistics dataset.

Figure 5B:
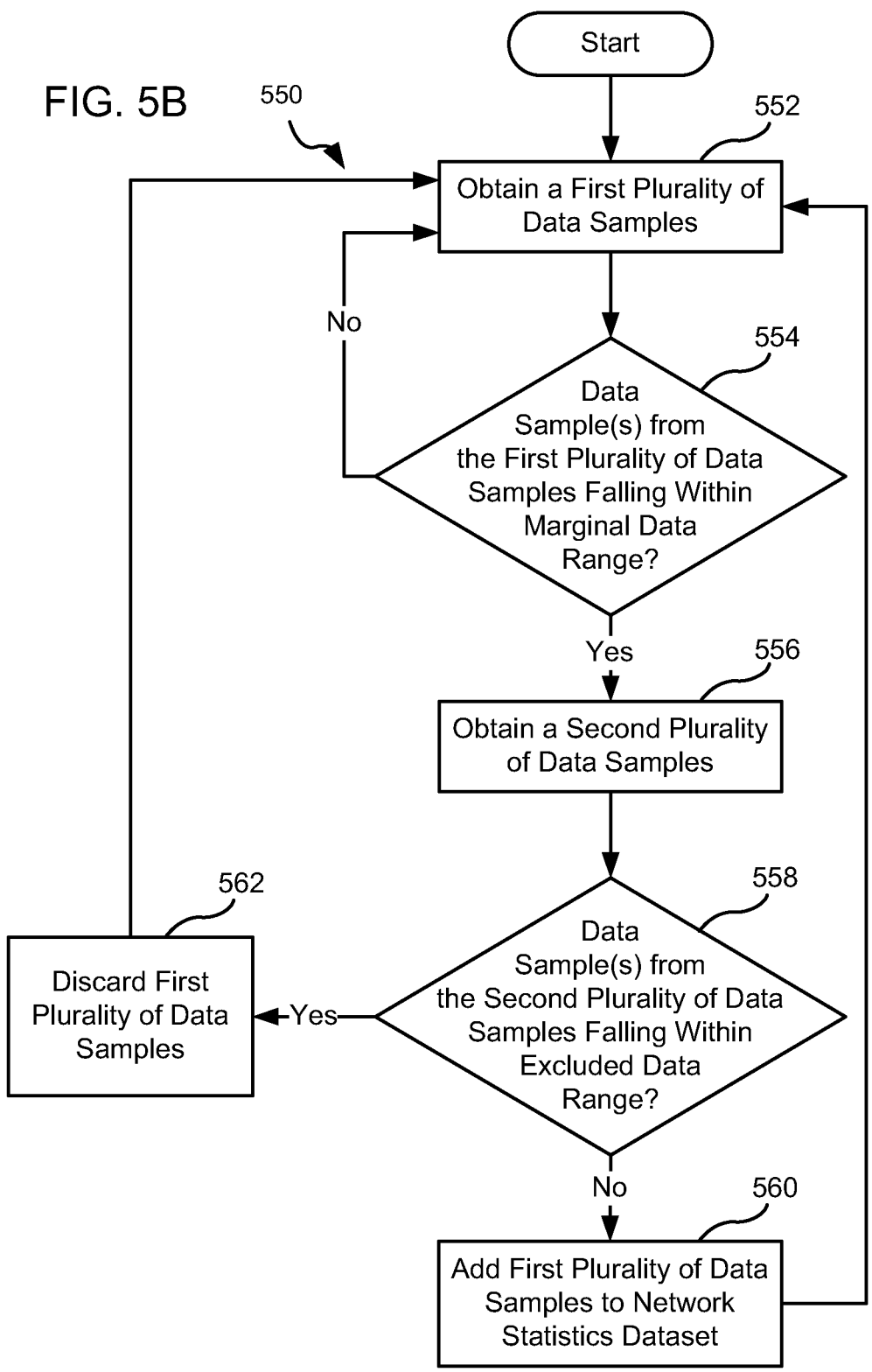
FIG. 5B illustrates one embodiment of a method for processing data samples that fall within a marginal data range.

FIG. 5B illustrates one embodiment of a method 550 for processing data samples that fall within a marginal data range. As discussed above, a marginal data range may be defined between an upper threshold and a lower threshold (e.g., the 90th percentile and the 70th percentile in FIG. 5A). At 552 a first plurality of data samples are obtained, and at 554, method 550 determines whether one or more data samples from the first plurality of data samples falls within the marginal data range. If so, a second plurality of data samples are obtained, at 556. At 558, the second plurality of data samples are analyzed to determine whether data samples from the second plurality of data samples fall within the excluded range. If so, the first plurality of data samples is discarded at 562. If no data samples from the second plurality of data samples fall within the excluded data range, the first plurality of data samples may be added to the network statistics dataset, at 560. In an alternative embodiment, upon receipt of each new sample the network statistics dataset is re-calculated based on the history of all samples collected since the start of the session, a trailing number of minutes, or sample set size.

Figure 6:
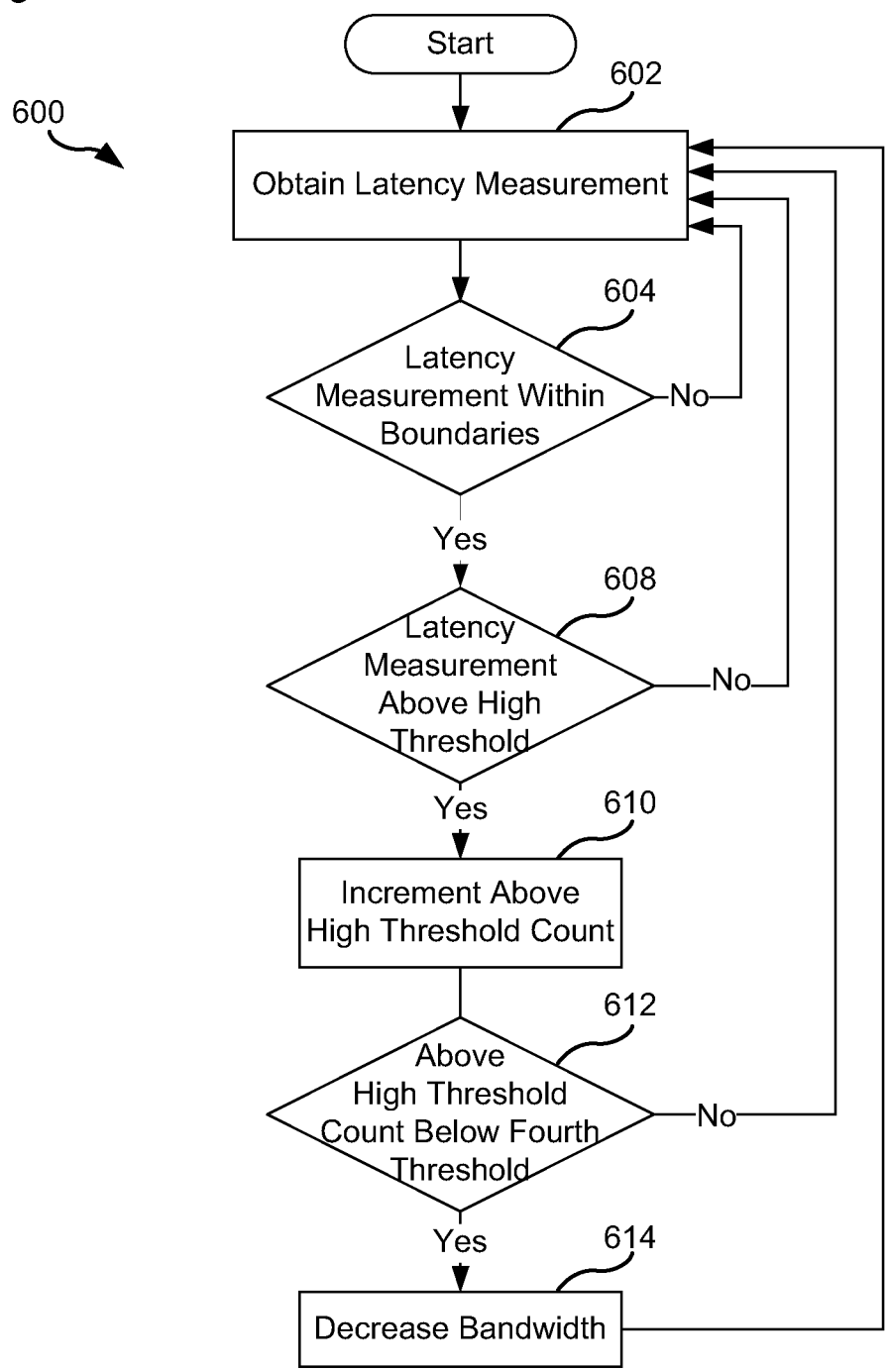
FIG. 6 illustrates one embodiment of a method for dynamically allocating bandwidth in a videoconferencing system.

FIG. 6 illustrates one embodiment of a method 600 for dynamically allocating bandwidth in a videoconferencing system. Method 600 illustrates an embodiment utilizing latency as a metric for evaluating network conditions. At 602, a latency measurement is obtained. It may be determined whether the obtained latency measurement is within specified boundaries, at 604. As discussed above, in connection with FIG. 5, measurements falling outside of specified ranges (e.g., above the 90th percentile) may be discarded. If the measurement falls outside of the specified boundaries, method 600 may return to 602 and obtain a new latency measurement. According to one embodiment, an increase in bandwidth may occur if a specified period of time has passed and no latency measurements have exceeded the high threshold. In this embodiment, the system presumes that because a network has remained stable for a specified time, additional bandwidth may be utilized.

It may be determined at 608 whether the latency measurement is above a high threshold. A latency measurement exceeding the high threshold may be indicative of a network disruption. Accordingly, at 610, an above high threshold count may be incremented. At 612, the above high threshold count may be compared to a fourth threshold. A fourth threshold may specify the number of above high threshold events that are detected before decreasing bandwidth, at 614.

Figure 7:
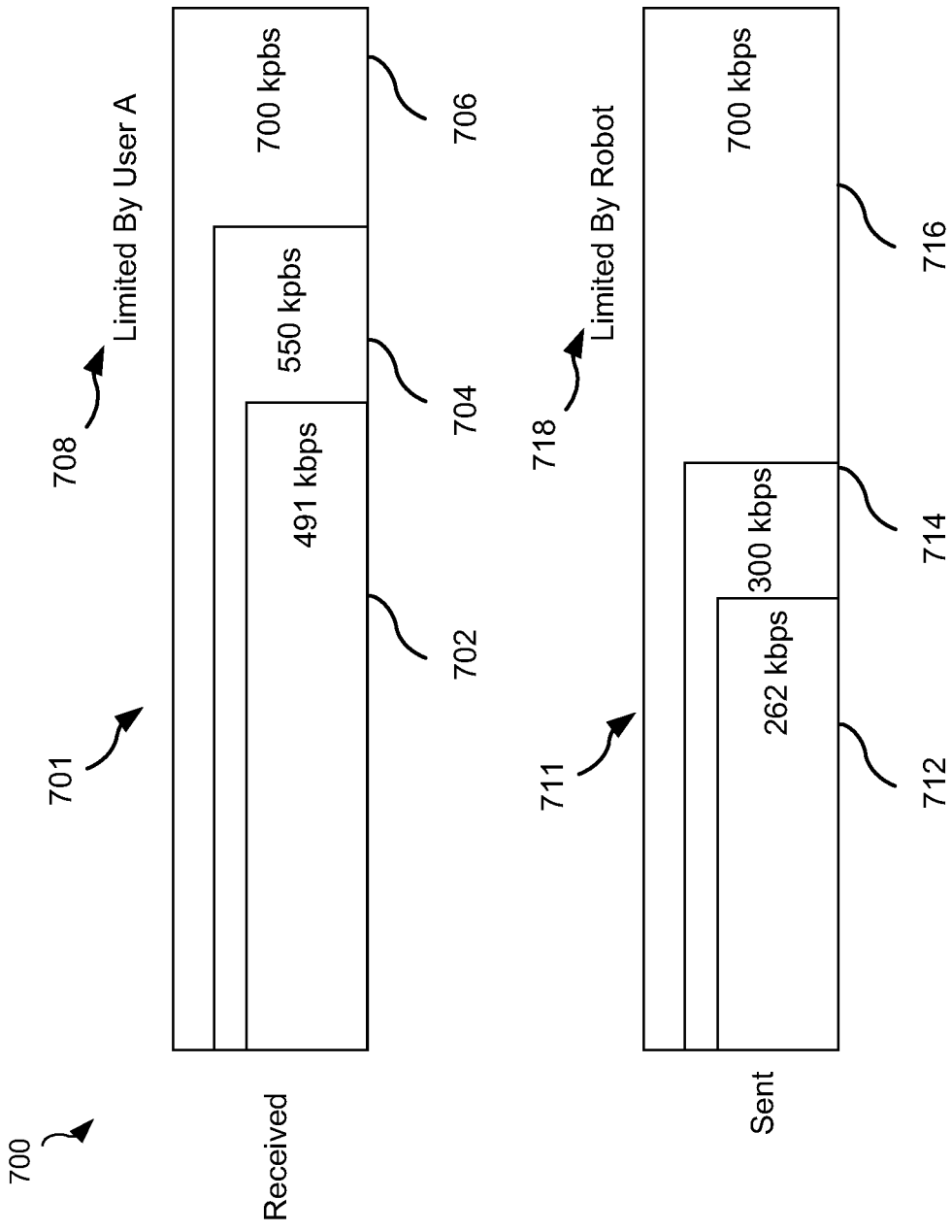
FIG. 7 illustrates a graphical user interface for displaying bandwidth utilization and dynamically established incoming and outgoing maximum bandwidth thresholds.

FIG. 7 illustrates a graphical user interface 700 for displaying bandwidth utilization and dynamically established incoming and outgoing maximum bandwidth thresholds. According to various embodiments, one or more videoconferencing endpoints may display graphical user interface 700. Information regarding data being received may be displayed by a first bar graph 701, while information regarding data being sent may be displayed by a second bar graph 711. Each of bar graphs 701 and 711 may show a first bar 702 and 712, respectively, which illustrate a current data transmission rate. Bar graphs 701 and 711 may also show a second bar 704 and 714, respectively, which illustrate bandwidth allocation. Bars 702 and 712 are less than or equal to the bandwidth allocation shown by bar 704 and 714. Bar graphs 701 and 711 may also illustrate a maximum throughput 706 and 716, respectively, based on the network connection between two or more videoconferencing endpoints.

Bar graphs 701 and 711 may also include an indication 708 and 718, respectively, that shows a limiting component in the network. For example, a multicasting session might include a local user, User A (a remote user), and a robotic videoconferencing endpoint. The data transmission rate from the robotic videoconferencing endpoints may be limited to the minimum value that can be sent or received from the other videoconferencing endpoints. In the illustrated embodiment, the limit for receiving data is imposed by User A, while the limit for transmitting data is imposed by the robotic videoconferencing endpoint. In one embodiment, the designated limiting endpoint may only be displayed when a mouse cursor is hovered over the related bar graph.

Figure 8:
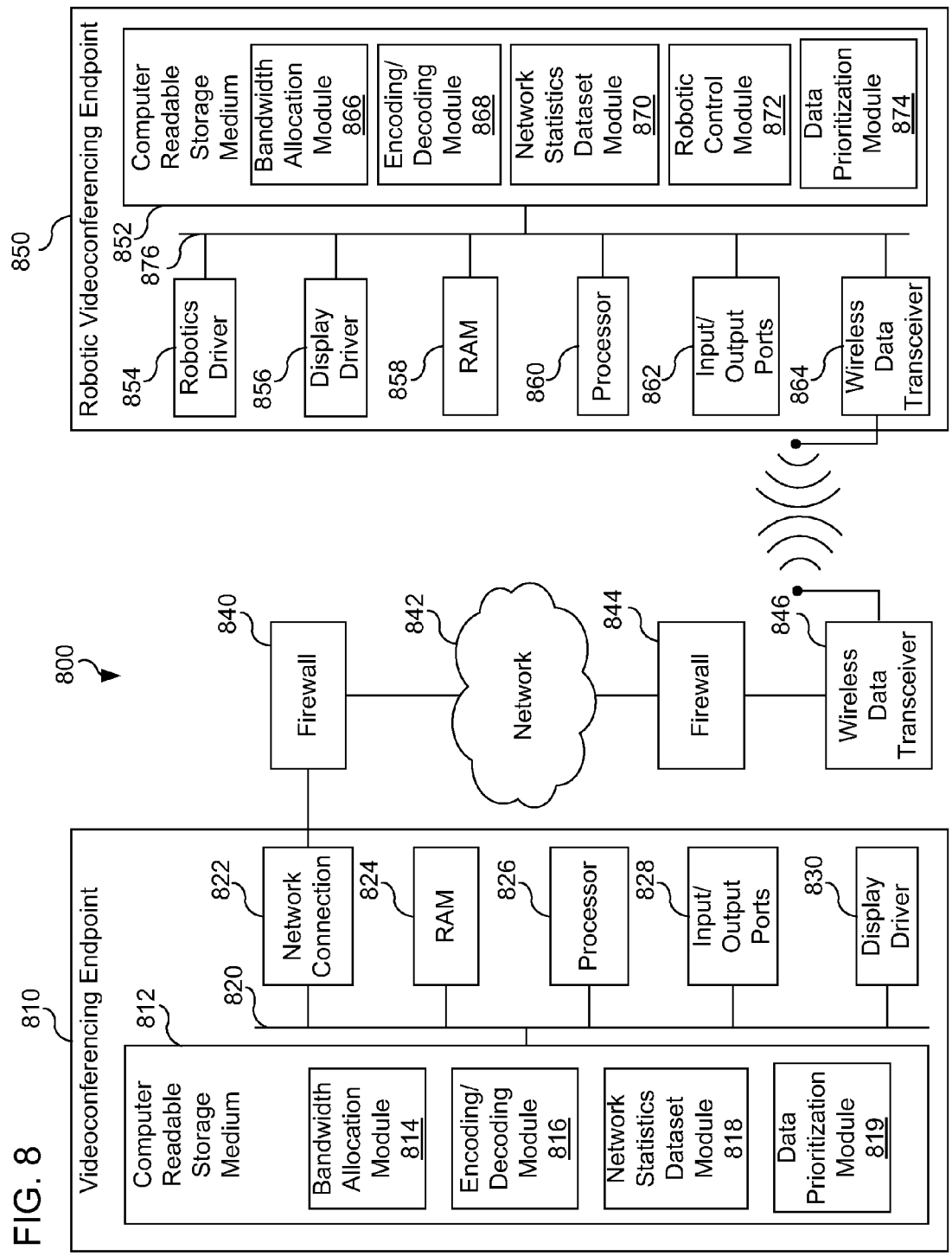
FIG. 8 illustrates a functional block diagram of a videoconferencing endpoint.

FIG. 8 illustrates a functional block diagram of one embodiment of a system 800, including a videoconferencing endpoint 810 and a robotic videoconferencing endpoint 850. System 800 allows videoconferencing endpoint 810 to exchange video, audio, and other types of data with robotic videoconferencing endpoint 850.

Videoconferencing endpoint 810 includes a network connection 822, Random Access Memory (RAM) 824, processor 826, input/output ports 828, a display driver 830, a computer readable storage medium 812, and a bus 820. Bus 820 provides a connection between network connection 822, RAM 824, processor 826, and computer readable storage medium

812. Processor 826 may be embodied as a general purpose processor, an application specific processor, a microcontroller, a digital signal processor, or other similar device. Processor 826 performs logical and arithmetic operations based on program code stored within RAM 824 and/or computer readable storage medium 812.

Network connection 822 may be configured to communicate with robotic videoconferencing endpoint by way of one or more network components, such as firewall 840, network 842, firewall 844, and wireless data transceiver 846. Network connection 822 may facilitate communication using any number of available protocols and/or physical media. Network 842 may comprise an intranet, a virtual private network, or a public network, such as the Internet or other data communications networks (e.g., cellular data networks). Firewalls 840 and 844 may be disposed between videoconferencing endpoints 810 and 850. According to various embodiments, network management techniques may be utilized to successfully route data from videoconferencing endpoint 810 to robotic videoconferencing endpoint 850.

Input/output ports 828 may be configured to allow videoconferencing endpoint 810 to utilize a wide variety of peripheral devices, some of which may generate data to be transmitted to robotic videoconferencing endpoint 850. For example, peripheral devices which may be utilized may include a video camera, a microphone, a device for controlling the movement of robotic videoconferencing endpoint 850, a keyboard, a mouse, and other such devices. Input/output ports 828 may comprise a variety of types of ports, such as USB, serial, parallel, IEEE 1394, and the like.

Display driver 830 may facilitate the generation of video images to be displayed to a user videoconferencing endpoint 810. Display driver 830 may, according to various embodiments, generate video data received from robotic videoconferencing endpoint 850 and display such data to a user. Display driver 830 may also be responsible for interfacing with other display devices, for example a touch screen.

Computer readable storage medium 812 may comprise various modules for communicating with robotic videoconferencing endpoint 850. Such modules may include a bandwidth allocation module 814, and encoding/decoding module 816, a network statistics dataset module 818, and a data prioritization module 819. Each module may perform one or more tasks associated with communication with robotic video endpoint 850 and/or management of such communications. In alternative embodiments, more or fewer modules than are shown in FIG. 8 may be utilized.

Bandwidth allocation module 814 may be configured to monitor and dynamically adjust the bandwidth utilized for transmission of data between videoconferencing endpoint 810 and robotic videoconferencing endpoint 850. As discussed above, a variety of methods may be utilized for dynamically allocating and adjusting bandwidth. Bandwidth allocation module 814 may be configured to implement the various methods for bandwidth allocation disclosed herein. Bandwidth allocation module 814 may further be configured to generate a graphical user interface display, such as illustrated in FIG. 7, for displaying bandwidth utilization and dynamically established incoming and outgoing maximum bandwidth thresholds.

Encoding/decoding module 816 may be configured to encode and/or decode video data, audio data, control data, and status data exchanged between videoconferencing endpoint 810 and robotic videoconferencing endpoint 850. According to various embodiments, encoding/decoding module 816 may be configured to adjust the video frame rate, image quality, compression ratios, and other characteristics of data to be transmitted in order to conform data transmission rates to an allocated bandwidth. According to one particular embodiment, encoding/decoding module 816 may adjust a video frame rate prior to segmenting the data into data packets.

Network statistics dataset module 818 may be configured to generate a network statistics dataset and to selectively add data to the network statistics dataset. Various embodiments for generating and adding data to the network statistics dataset are disclosed herein, and network statistics dataset module 818 may be configured to perform the features described in connection with such embodiments.

Data prioritization module 819 may be configured to prioritize various types of data to be transmitted between videoconferencing endpoint 810 robotic videoconferencing endpoint 850. According to various embodiments, a variety of data prioritization schemes may be employed so that higher priority data is transmitted with greater reliability or at a higher data rate than lower priority data. For example, in system 800 control data transmitted from videoconferencing endpoint 810 to robotic videoconferencing endpoint 850 may be designated as high priority data. Such a prioritization may allow a user to remain in control of the motion of robotic videoconferencing endpoint 850 even if network throughput is reduced. Status data, which may include telemetry data gathered from a patient (e.g., pulse rate, EKG, oxygenation, etc.), may also be designated as relatively high priority data. Audio data may be prioritized before video data, such that a medical practitioner and patient can maintain audible communication in spite of decreases in network throughput. Finally, video data may be transmitted using the lowest priority.

According to various embodiments, videoconferencing endpoint 810 may be embodied as a general purpose computer including particular software and/or configured to interface with robotic videoconferencing endpoint 850. Such software may be delivered as a computer program product. Hardware resources facilitating communication with and/or control of robotic videoconferencing endpoint 850 may, according to various embodiments, comprise an audio and/or video input device coupled to input/output ports 828, or an input device specifically configured to control one or more robotic elements of robotic videoconferencing endpoint 850.

Robotic videoconferencing endpoint 850 includes a robotics driver 854, a display driver 856, RAM 858, a processor 860, input/output ports 862, a wireless data transceiver 864, a computer readable storage medium 852, and a bus 876. The function of display driver 856, RAM 858, and processor 860 may be similar to the functions described in connection with corresponding structures in videoconferencing endpoint 810. Input/output ports 862 may further be configured to receive telemetry data from a variety of sensors, which may be utilized to monitor various physical conditions. In one particular embodiment, where robotic videoconferencing endpoint 850 is utilized in a telemedicine application, input/output ports 862 may be configured to interface with a variety of medical sensors (e.g., pulse rate sensor, an EKG sensor, a blood oxygenation sensor, etc.).

Robotics driver 854 may be configured to receive and implement instructions for moving robotic videoconferencing endpoint 850. Such instructions may include driving robotic videoconferencing endpoint 850 from one place to another, manipulating one or more robotic arms, and the like.

Wireless data transceiver 864 may be configured to exchange data wirelessly with wireless data transceiver 846. Data may be exchanged according to a variety of wireless protocols, including but not limited to the IEEE 802.11 protocols and cellular data transmission protocols.

Computer readable storage medium 852 may comprise various modules for communicating with videoconferencing endpoint 810. Such modules may include a bandwidth allocation module 866, and encoding/decoding module 868, a network statistics dataset module 870, a robotic control module 872, and a data prioritization module 874. The functions of bandwidth allocation module 866, encoding/decoding module 868, network statistics dataset module 870, and data prioritization module 874 may be similar to corresponding modules, which are described above in connection with videoconferencing endpoint 810.

Robotic control module 872 may operate in conjunction with robotics driver 854 to facilitate control of robotic videoconferencing endpoint 850. Robotic control module 872 may be configured, according to various embodiments, to interact with one or more devices associated with videoconferencing endpoint 810 and to receive instruction from such device that allows a remote user to control robotic videoconferencing endpoint 850.

Many changes may be made to the details of the above-described embodiments without departing from the underlying principles of the present disclosure. The scope of the present invention should, therefore, be determined only by the following claims.

The invention claimed is:

1. A mobile videoconferencing endpoint, comprising:
   a bus;
   a wireless network transceiver in communication with the bus and configured to wirelessly communicate data with a network;
   a processor in communication with the bus;
   a robotic element in communication with the bus;
   a robotics driver in communication with the bus and configured to receive an instruction for controlling the robotic element via the wireless network transceiver and to control the robotic element according to the instruction for controlling the robotic element;
   a video input source in communication with the bus;
   an audio input source in communication with the bus; and
   a computer readable storage medium in communication with the bus, comprising:
   a network statistics dataset module executable on the processor and configured to generate a network statistics dataset, and configured to compare a plurality of data samples to the network statistics dataset, each of the plurality of data samples comprising a quantifiable metric representing one or more network conditions;
   a bandwidth allocation module executable on the processor and configured to dynamically adjust a data communication bandwidth between the videoconferencing endpoint and the network based upon comparison of the plurality of data samples to the network statistics dataset; and,
   a data prioritization module executable on the processor and configured to prioritize data based upon classifying the data as one of a plurality of types of data, wherein the data prioritization module prioritizes an audio data type over a video data type.

2. The videoconferencing endpoint of claim 1, wherein the data prioritization module operates at an application layer and is in communication with the bandwidth allocation module.

3. The videoconferencing endpoint of claim 2, wherein the plurality of types of data comprise video data, audio data, control data, and status data.

4. The videoconferencing endpoint of claim 1, comprising: a patient sensor interface in communication with the bus and configured to receive information from a patient sensor and to transmit information received from the patient sensor via the wireless network transceiver.

5. The videoconferencing endpoint of claim 1, wherein the computer readable storage medium further comprises:
   an encoding module executable on the processor and configured to encode at least one of audio and video data, such that total data transmitted from the videoconferencing endpoint is less than a portion of the data communication bandwidth allocated for transmitting data.

6. The videoconferencing endpoint of claim 5, wherein the encoding module encodes audio and video data, and the encoding module is further configured to adjust at least one of a frame rate and a resolution of video data.

7. The videoconferencing endpoint of claim 5, wherein the encoding module encodes audio and video data, and the encoding module is further configured to adjust at least one of a video frame rate, a video compression ratio, an audio compression ratio and the resolution of video data, such that a data transmission rate is less than the difference between a portion of the data communication bandwidth allocated for transmission of data by the videoconferencing endpoint and a combined data transmission rate of audio data and status data.

8. The videoconferencing endpoint of claim 1, wherein the plurality of data samples comprise a plurality of latency measurements associated with transmission of data on the network.

9. The videoconferencing endpoint of claim 1, wherein the bandwidth allocation module is further configured to establish a minimum allowable data communication bandwidth.

10. The videoconferencing endpoint of claim 9, wherein the bandwidth allocation module is further configured to establish a first minimum allowable data communication bandwidth, and wherein the data communication bandwidth between the videoconferencing endpoint and the network exceeds the minimum allowable data communication bandwidth.

11. The videoconferencing endpoint of claim 10, wherein the bandwidth allocation module is further configured to receive a second minimum allowable data communication bandwidth associated established by a remote videoconferencing endpoint.

12. The videoconferencing endpoint of claim 11, wherein the first minimum allowable data communication bandwidth and the second minimum allowable data communication bandwidth are asymmetrical.

13. The videoconferencing endpoint of claim 1, wherein the bandwidth allocation module is further configured to display a first graphical indicator representing an estimated data communication bandwidth capacity between the video conferencing endpoint and the network; and to display a second graphical indicator representing a current data transmission rate, the current data transmission rate being less than the estimated data communication bandwidth capacity between the video conferencing endpoint and the network.

\* \* \* \* \*